United States Patent [19]

Beria et al.

[11] Patent Number: 5,753,629
[45] Date of Patent: May 19, 1998

[54] DISTAMYCIN A ANALOGUES AS ANTITUMOUR OR ANTIVIRAL AGENTS

[75] Inventors: Italo Beria, Villamarzana; Enrico Pesenti, Cologno Monzese; Laura Capolongo; Nicola Mongelli, both of Milan; Pier Giovanni Baraldi, Ferrara, all of Italy

[73] Assignee: Pharmacia S.p.A., Milan, Italy

[21] Appl. No.: 612,836

[22] PCT Filed: Jul. 18, 1995

[86] PCT No.: PCT/EP95/02814

§ 371 Date: Mar. 18, 1996

§ 102(e) Date: Mar. 18, 1996

[87] PCT Pub. No.: WO96/05196

PCT Pub. Date: Feb. 22, 1996

[30] Foreign Application Priority Data

Aug. 8, 1994 [GB] United Kingdom ............ 9416005

[51] Int. Cl.[6] ............... A61K 38/00; C07K 5/00
[52] U.S. Cl. .................. 514/18; 514/19; 514/422; 530/330; 530/331; 548/518
[58] Field of Search ................. 514/18, 19, 422; 530/330, 331; 548/518

[56] References Cited

FOREIGN PATENT DOCUMENTS

| A0246 868 | 11/1987 | European Pat. Off. . |
| A0388 948 | 9/1994 | European Pat. Off. . |
| A36 23 880 | 1/1987 | Germany . |

OTHER PUBLICATIONS

Abstract 1971:74952 De Ratuld et al, Progr. Antimicrob. Anticancer Chemo. Proc. Int. Cong. Chemoth. 6th Mtg Date 1969 vol. 2 14–19.

WO, A, 94 25436, Nov. 10, 1994.

WO, A, 94 20463, Sep. 15, 1994.

J. Med. Chem., vol. 32, No. 4, 1989, pp. 774–778, Arcamone et al, "Synthesis, DNA–binding properties, and antitumor activity of . . . ".

Bioorg. Med. Chem., vol. 4, No. 12, 1994, pp. 1467–1472, D'Alessio et al., "Structure–activity relationship of novel distamycin A derivatives: . . . ".

*Primary Examiner*—Cecilia J. Tsang
*Assistant Examiner*—Bennett Celsa
*Attorney, Agent, or Firm*—Nikaido Marmelstein Murray & Oram, LLP

[57] ABSTRACT

The present invention relates to compounds of formula (I)

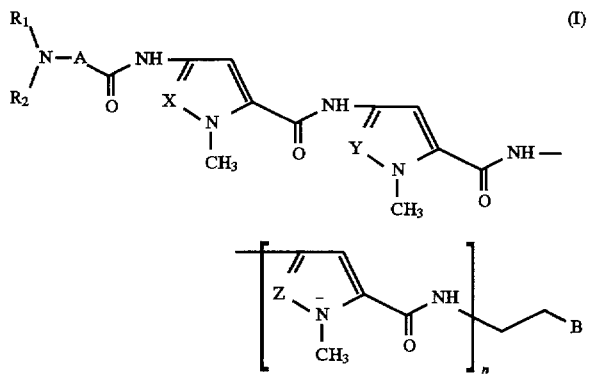

The compounds of the invention are useful as antitumor or antiviral agents.

12 Claims, No Drawings

DISTAMYCIN A ANALOGUES AS ANTITUMOUR OR ANTIVIRAL AGENTS

This application is a 371 of PCT/EPA/02814 filed Jul. 18, 1995.

BACKGROUND OF THE INVENTION

The invention relates to new peptidic compounds analogous to Distamycin A, to a process for their preparation, to pharmaceutical compositions containing them and to their use as therapeutic agents.

Distamycin A is an antibiotic substance with antiviral and oncolytic properties, having a polypyrrole framework (Nature 203, 1064 (1964); J. Med. Chem. 32, 774–778 (1989)).

The peptidic compounds of the invention are analogous to Distamycin A wherein the pyrrole rings are substituted partially or completely by other heteromonocyclic rings.

Analogous of Distamycin A, Netropsin or Lexitropsin wherein one or more pyrrole rings are substituted by a 1,2,4-triazole ring are reported, for example, in Chem. Res. Toxicol. 4, 241–252 (1991) and Heterocycles Vol. 31, 1629 (1990).

Distamycin derivatives wherein a pyrrole ring is substituted by a thiazole ring are reported in Anti-Cancer Drug Design 5, 3–20 (1990) and J. Org. Chem. 55, 728–737 (1990).

Distamycin derivatives wherein a pyrrole ring is substituted by an imidazole ring are reported in Anti-Cancer Drug Design 8, 173–192 (1993) and J. Am. Chem. Soc. Vol. 114, 5911–5919 (1992).

Distamycin derivatives wherein a pyrrole ring is substituted by a pyrazole ring are reported in Anti-Cancer Drug Design 6, 501–517 (1991).

SUMMARY OF THE INVENTION

The present invention relates to compounds of the following formula (I)

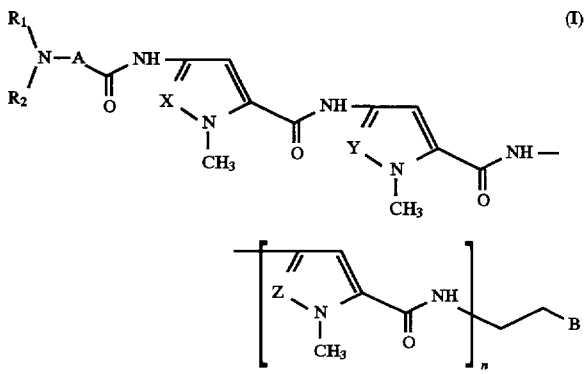

wherein n is 0 or 1;

each of X, Y, Z is independently N or CH;

A is a pentatomic heteromonocyclic ring unsubstituted or substituted by a $C_1$–$C_3$ alkyl group;

B is

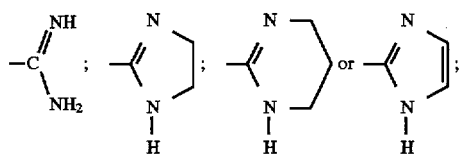

and either $R_1$ and $R_2$ are the same and they are both a $C_1$–$C_6$ alkyl group unsubstituted or substituted by halogen or hydroxy; or one of $R_1$ and $R_2$ is hydrogen and the other is a group

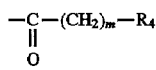

in which m is zero or an integer of 1 to 4 and $R_4$ is aziridinyl; cyclopropyl; a vinyl group unsubstituted or substituted in position 1 or 2 by halogen or $C_1$–$C_3$ alkyl; an oxyranyl group unsubstituted or substituted in position 2 by a $C_1$–$C_3$ alkyl or halogen; or a group

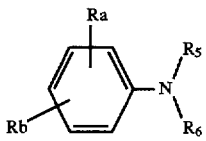

in which $R_5$ and $R_6$ are both a $C_1$–$C_6$ alkyl group unsubstituted or substituted by a halogen or hydroxy group, each of $R_a$ and $R_b$ independently is hydrogen, $C_1$–$C_3$ alkyl or $C_1$–$C_3$ alkoxy, provided that:

a) when each of X, Y, Z is CH, then A is not thiophene or pyrrole unsubstituted or substituted by a $C_1$–$C_3$ alkyl group; and b) when n is 1, each of X, Y, Z is CH and $R_1$ and $R_2$ are the same and they are 2-chloroethyl, then A is not 1-methylimidazole or thiazole; and the pharmaceutically acceptable salt thereof.

The invention includes also all the possible isomers covered by formula (I), both separately and in mixture.

The alkyl groups may be branched or straight chain.

A pentatomic heteromonocyclic ring is preferably a pentatomic saturated or unsaturated, most preferably unsaturated, heteromonocyclic ring containing one or two or three heteroatoms chosen from S or N.

An unsubstituted pentatomic heteromonocyclic ring is, for example, thiophene, thiazole, imidazole, pyrrole, pyrazole, 1,2,4-triazole.

A pentatomic heteromonocyclic ring substituted by $C_1$–$C_3$ alkyl is, for example, 1-methylpyrazole, 1-methyl-1,2,4- triazole, 1-methylpyrrole and 1-methylimidazole.

The imidazole and pyrrole rings are preferably linked in position 2 to the

group and in position 4 to the —NH— group.

The thiazole rings are preferably linked in position 2 to the —N— and in position 4 to the —CO— group.

The pyrazole and the 1,2,4-triazole rings are preferably linked in position 3 to the —N— group and in position 5 to the —CO— group.

A $C_1$–$C_6$ alkyl group is preferably a $C_1$–$C_3$ alkyl group, for example methyl, ethyl.

A halogen atom is preferably chlorine, bromine or fluorine.

When $R_1$ and $R_2$ are both a $C_1$–$C_6$ alkyl group they are preferably a $C_1$–$C_3$ alkyl group, for example methyl and ethyl.

When $R_1$ and $R_2$ are both a $C_1$–$C_6$ alkyl group substituted by halogen they are preferably 2-chloroethyl, 2-bromoethyl, 2-fluoroethyl.

When $R_1$ and $R_2$ are both a $C_1$–$C_6$ alkyl group substituted by hydroxy, they are preferably 2-hydroxyethyl.

When one of $R_1$ and $R_2$ is a group

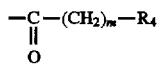

in which m is zero or an integer of 1 to 4, $R_4$ is preferably aziridinyl, cyclopropyl, αbromovinyl, α-chlorovinyloxyranyl, 2-fluoroxyranyl, 2-methyloxyranyl,

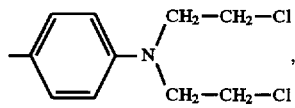

or

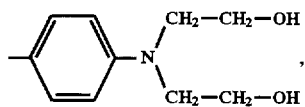

or

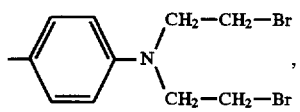

Pharmaceutically acceptable salts of the compounds of formula (I) are their salts with pharmaceutically acceptable, either inorganic or organic, acids.

Examples of inorganic acids are hydrochloric, hydrobromic, sulfuric and nitric acid; examples of organic acids are acetic, propionic, succinic, malonic, citric, tartaric, methanesulfonic and p-toluenesulfonic acid.

DETAILED DESCRIPTION OF PREFERRED EMBODIMENTS OF THE INVENTION

A preferred class of compounds of the invention are the compounds of formula (I) wherein:

n is 0 or 1; each of X, Y, Z independently is N or CH;

A is thiazole, imidazole, 1,2,4-triazole, 1-methyl-pyrrole, 1-methylimidazole or 1-methylpyrazole;

B is

and either $R_1$ and $R_2$ are the same and they are both 2-chloroethyl, 2-fluoroethyl, 2-bromoethyl or one of $R_1$ and $R_2$ is hydrogen and the other is α-bromoacryloyl, 4-N,N-bis(2-chloroethyl)amino-benzene-1-carbonyl, 4-N,N-bis(2-bromoethyl)amino-benzene-1-carbonyl, provided that:

a) when each of X, Y, Z is CH, then A is not 1-methylpyrrole; and b) when n is 1, each of X, Y, Z is CH and $R_1$ and $R_2$ are the same and they are both 2-chloroethyl, then A is not 1-methylimidazole or thiazole, and the pharmaceutically acceptable salts thereof.

A particularly preferred class of compounds of the invention are the compounds of formula (I) wherein:

n is 0 or 1; each of X, Y, Z independently is N or CH;

A is 1-methyl-pyrrole or 1-methylpyrazole;

B is

and either $R_1$ and $R_2$ are the same and they are both 2-chloroethyl, 2-fluoroethyl, 2-bromoethyl or one of $R_1$ and $R_2$ is hydrogen and the other is α-bromoacryloyl, 4-N,N-bis(2-chloroethyl)amino-benzene-1-carbonyl, 4-N,N-bis(2-bromoethyl)amino-benzene-1-carbonyl.

Examples of specific compounds under this invention are the following compounds:

1) β-[1-methyl-4-[1-methyl-4-[1-methyl-3-[4-N,N-bis(2-chloroethyl)amino-benzene-1-carboxamido)pyrazole-5-carboxamido]pyrrole-2-carboxamido]pyrrole-2-carboxamido]propionamidine;

2) β-[1-methyl-4-[1-methyl-4-[2-[4-N,N-bis(2-chloroethyl)amino-benzene-1-carboxamido]thiazole-4-carboxamido]pyrrole-2-carboxamido]pyrrole-2-carboxamido]propionamidine;

3) β-[1-methyl-3-[1-methyl-4-[1-methyl-4-[4-N,N-bis(2-chloroethyl)amino-benzene-1-carboxamido]pyrrole-2-carboxamido]pyrrole-2-carboxamido]pyrazole-5-carboxamido]propionamidine;

4) β-[1-methyl-3-[1-methyl-3-[1-methyl-4-[4-N,N-bis(2-chloroethyl)amino-benzene-1-carboxamido]pyrrole-2-carboxamido]pyrazole-5-carboxamido]propionamidine;

5) β-[1-methyl-3-[1-methyl-4-[2-[4-N,N-bis(2-chloroethyl)amino-benzene-1-carboxamido]thiazole-4-carboxamido]pyrrole-2-carboxamido]pyrazole-5-carboxamido]propionamidine;

6) β-[1-methyl-4-[1-methyl-4-[3-[4-N,N-bis(2-chloroethyl)amino-benzene-1-carboxamido]-1,2,4-triazole-5-carboxamido]pyrrole-2-carboxamido] pyrrole-2-carboxamido]propionamidine;

7) β-[1-methyl-3-[1-methyl-3-[1-methyl-3-[4-N,N-bis(2-chloroethyl)amino-benzene-1-carboxamido]pyrazole-5-carboxamido]pyrazole-5-carboxamido]pyrazole-5-carboxamido]propionamidine;

8) β-[1-methyl-4-[1-methyl-4-[1-methyl-4-[4-N,N-bis(2-chloroethyl)amino-benzene-1-carboxamido]imidazole-2-carboxamido]pyrrole-2-carboxamido]pyrrole-2-carboxamido]propionamidine;

9) β-[1-methyl-4-[1-methyl-3-[1-methyl-4-[4-N,N-bis(2-chloroethyl)amino-benzene-1-carboxamido]imidazole-2-carboxamido]pyrazole-5-carboxamido]pyrrole-2-carboxamido]propionamidine;

10) β-[1-methyl-4-[1-methyl-3-[3-[4-N,N-bis(2-chloroethyl)amino-benzene-1-carboxamido]-1,2,4-triazole-5-carboxamido]pyrazole-5-carboxamido] pyrrole-2-carboxamido]propionamidine;

11) β-[1-methyl-3-[1-methyl-3-[1-methyl-4-[4-N,N-bis(2-chloroethyl)amino-benzene-1-carboxamido]

12) β-[1-methyl-3-[1-methyl-3-[3-[4-N,N-bis(2-chloroethyl)amino-benzene-1-carboxamido]-1,2,4-triazole-5-carboxamido]pyrazole-5-carboxamido]pyrazole-5-carboxamido]propionamidine;

13) β-[1-methyl-4-[1-methyl-4-[1-methyl-4-[1-methyl-3-[4-N,N-bis(2-chloroethyl)amino-benzene-1-carboxamido]pyrazole-5-carboxamido]pyrrole-2-carboxamido]pyrrole-2-carboxamido]pyrrole-2-carboxamido]propionamidine;

14) β-[1-methyl-3-[1-methyl-3-[1-methyl-4-[1-methyl-3-[4-N,N-bis(2-chloroethyl)amino-benzene-1-carboxamido]pyrazole-5-carboxamido]pyrrole-2-carboxamido]pyrazole-5-carboxamido]pyrazole-5-carboxamido]propionamidine;

15) β-[1-methyl-3-[1-methyl-3-[1-methyl-3-[1-methyl-3-[4-N,N-bis(2-chloroethyl)amino-benzene-1-carboxamido]pyrazole-5-carboxamido]pyrazole-5-carboxamido]pyrazole-5-carboxamido]pyrazole-5-carboxamido]propionamidine;

16) β-[1-methyl-4-[1-methyl-4-[2(α-bromoacrylamido)thiazole-4-carboxamido]pyrrole-2-carboxamido]pyrrole-2-carboxamido]propionamidine;

17) β-[1-methyl-4-[1-methyl-4-[1-methyl-3-[α-bromoacrylamido)pyrazole-5-carboxamido]pyrrole-2-carboxamido]pyrrole-2-carboxamido]propionamidine;

18) β-[1-methyl-4-[1-methyl-4-[3-(α-bromoacrylamido)-1,2,4-triazole-5-carboxamido]pyrrole-2-carboxamido]pyrrole-2-carboxamido]propionamidine;

19) β-[1-methyl-3-[1-methyl-3-[1-methyl-4-(α-bromoacrylamido)pyrrole-2-carboxamido]pyrazole-5-carboxamido]pyrazole-5-carboxamido]propionamidine;

20) β-(1-methyl-3-[1-methyl-4-[1-methyl-4-(α-bromoacrylamido)pyrrole-2-carboxamido]pyrrole-2-carboxamido]pyrazole-5-carboxamido]propionamidine;

21) β-[1-methyl-3-[1-methyl-4-[2-(α-bromoacrylamido)thiazole-4-carboxamido]pyrrole-2-carboxamido]pyrazole-5-carboxamido]propionamidine;

22) β-[1-methyl-4-[1-methyl-4-[1-methyl-4-(α-bromoacrylamido)imidazole-2-carboxamido]pyrrole-2-carboxamido]pyrrole-2-carboxamido]propionamidine;

23) β-[1-methyl-3-[1-methyl-3-[1-methyl-3-(α-bromoacrylamido)pyrazole-5-carboxamido]pyrazole-5-carboxamido]pyrazole-5-carboxamido]propionamidine;

24) β-[1-methyl-4-[1-methyl-3-[1-methyl-4-(α-bromoacrylamido)imidazole-2-carboxamido]pyrazole-5-carboxamido]pyrrole-2-carboxamido]propionamidine;

25) β-[1-methyl-4-[1-methyl-3-[3-(α-bromoacrylamido)-1,2,4-triazole-5-carboxamido]pyrazole-5-carboxamido]pyrrole-2-carboxamido]propionamidine;

26) β-[1-methyl-4-[1-methyl-4-[1-methyl-3-[1-methyl-3-(α-bromoacrylamido)pyrazole-5-carboxamido]pyrazole-5-carboxamido]pyrrole-2-carboxamido]pyrrole-2-carboxamido]propionamidine;

27) β-[1-methyl-3-[1-methyl-3-[1-methyl-3-[1-methyl-3-(α-bromoacrylamido)pyrazole-5-carboxamido]pyrazole-5-carboxamido]pyrazole-5-carboxamido]propionamidine;

28) β-[1-methyl-4-[1-methyl-4-[1-methyl-4-[1-methyl-3-(α-bromoacrylamido)pyrazole-5-carboxamido]pyrrole-2-carboxamido]pyrrole-2-carboxamido]pyrrole-2-carboxamido]propionamidine;

29) β-[1-methyl-4-[1-methyl-4-[1-methyl-3-[1-methyl-3-[4-N,N-bis(2-chloroethyl)amino-benzene-1-carboxamido]pyrazole-5-carboxamido]pyrazole-5-carboxamido]pyrrole-2-carboxamido]pyrrole-2-carboxamido]propionamide;

30) β-[1-methyl-3-[1-methyl-3-[1-methyl-4-[1-methyl-4-[4-N,N-bis(2-chloroethyl)amino-benzene-1-carboxamido]imidazole-2-carboxamido]pyrrole-2-carboxamido]pyrazole-5-carboxamido]pyrazole-5-carboxamido]propionamidine;

31) β-[1-methyl-3-[1-methyl-3-[1-methyl-4-[3-[4-N,N-bis(2-chloroethyl)amino-benzene-1-carboxamido]1,2,4,triazole-5-carboxamido]pyrrole-2-carboxamido]pyrazole-5-carboxamido]pyrazole-5-carboxamido]propionamidine;

32) β-[1-methyl-3-[1-methyl-3-[1-methyl-4-[1-methyl-4-[4-N,N-bis(2-chloroethyl)amino-benzene-1-carboxamido]pyrrole-2-carboxamido]pyrrole-2-carboxamido]pyrazole-5-carboxamido]pyrazole-5-carboxamido]propionamidine;

33) β-[1-methyl-3-[1-methyl-4-[1-methyl-3-[4-N,N-bis(2-chloroethyl)amino-benzene-1-carboxamido]pyrazole-5-carboxamido]pyrrole-2-carboxamido]pyrazole-5-carboxamido]propionamidine;

34) β-[1-methyl-3-[1-methyl-4-[1-methyl-4-[4-N,N-bis(2-chloroethyl)amino-benzene-1-carboxamido]imidazole-2-carboxamido]pyrrole-2-carboxamido]pyrazole-5-carboxamido]propionamidine;

35) β-[1-methyl-3-[1-methyl-4-[3-[4-N,N-bis(2-chloroethyl)amino-benzene-1-carboxamido]1,2,4,triazole-5-carboxamido]pyrrole-2-carboxamido]pyrazole-5-carboxamido]propionamidine;

36) β-[1-methyl-3-[1-methyl-4-[1-methyl-4-[1-methyl-3-[4-N,N-bis(2-chloroethyl)amino-benzene-1-carboxamido]pyrazole-5-carboxamido]pyrrole-2-carboxamido]pyrrole-2-carboxamido]pyrazole-5-carboxamido]propionamidine; 37) β-[1-methyl-3-[1-methyl-4-[1-methyl-4-[1-methyl-4-[4-N,N-bis(2-chloroethyl)amino-benzene-1-carboxamido]imidazole-2-carboxamido]pyrrole-2-carboxamido]pyrrole-2-carboxamido]pyrazole-5-carboxamido]propionamidine;

38) β-[1-methyl-3-[1-methyl-4-[1-methyl-4-[3-[4-N,N-bis(2-chloroethyl)amino-benzene-1-carboxamido]1,2,4,triazole-5-carboxamido]pyrrole-2-carboxamido]pyrrole-2-carboxamido]pyrazole-5-carboxamido]propionamidine;

39) β-[1-methyl-3-[1-methyl-4-[1-methyl-4-[1-methyl-4-[4-N,N-bis(2-chloroethyl)amino-benzene-1-carboxamido]pyrrole-2-carboxamido]pyrrole-2-carboxamido]pyrrole-2-carboxamido]pyrazole-5-carboxamido]propionamidine;

40) β[1-methyl-3-[1-methyl-4-[1-methyl-3-[1-methyl-3-[4-N,N-bis(2-chloroethyl)amino-benzene-1-carboxamido]pyrazole-5-carboxamido]pyrazole-5-carboxamido]pyrrole-2-carboxamido]pyrazole-5-carboxamido]propionamidine;

41) β-[1-methyl-3-[1-methyl-4-[1-methyl-3-[1-methyl-4-[4-N,N-bis(2-chloroethyl)amino-benzene-1-carboxamido]pyrrole-2-carboxamido]pyrazole-5-carboxamido]pyrrole-2-carboxamido]pyrazole-5-carboxamido]propionamidine;

42) β-[1-methyl-3-[1-methyl-4-[1-methyl-3-[1-methyl-4-[4-N,N-bis(2-chloroethyl)amino-benzene-1-carboxamido]imidazole-2-carboxamido]pyrazole-5-carboxamido]pyrrole-2-carboxamido]pyrazole-5-carboxamido]propionamidine;

43) β-[1-methyl-3-[1-methyl-4-[1-methyl-3-[3-[4-N,N-bis(2-chloroethyl)amino-benzene-1-carboxamido]1,2,4,triazole-5-carboxamido]pyrazole-5-carboxamido]pyrrole-2-carboxamido]pyrazole-5-carboxamido]propionamidine;

44) β-(1-methyl-4-(1-methyl-4-(1-methyl-4(2-(α-bromoacrylamido)thiazole-4-carboxamido)pyrrole-2-carboxamido)pyrrole-2-carboxamido)pyrrole-2-carboxamido)propionamidine;

45) β-(1-methyl-4-(1-methyl-4-(1-methyl-4-(3-(α-bromoacrylamido)1,2,4,triazole-5-carboxamido)pyrrole-2-carboxamido)pyrrole-2-carboxamido)pyrrole-2-carboxamido)propionamidine;

46) β-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propionamidine;

47) β-(1-methyl-3-(1-methyl-3-(1-methyl-4-(α-bromoacrylamido)imidazole-2-carboxamido)pyrazole-5-carboxamido)pyrazole-5-carboxamido)propionamidine;

48) β-(1-methyl-3-(1-methyl-3-(2-(α-bromoacrylamido)thiazole-4-carboxamido)pyrazole-5-carboxamido)pyrazole-5-carboxamido)propionamidine;

49) β-(1-methyl-3-(1-methyl-3-(3-(α-bromoacrylamido)1,2,4,triazole-5-carboxamido)pyrazole-5-carboxamido)pyrazole-5-carboxamido)propionamidine;

50) β-(1-methyl-3-(1-methyl-3-(1-methyl-4-(1-methyl-3-(α-bromoacrylamido)pyrazole-5-carboxamido)pyrrole-2-carboxamido)pyrazole-5-carboxamido)pyrazole-5-carboxamido)propionamidine;

51) β-(1-methyl-3-(1-methyl-3-(1-methyl-4-(1-methyl-4-(α-bromoacrylamido)imidazole-2-carboxamido)pyrrole-2-carboxamido)pyrazole-5-carboxamido)pyrazole-5-carboxamido)propionamidine;

52) β-(1-methyl-3-(1-methyl-3-(1-methyl-4-(1-methyl-4-(α-bromoacrylamido)pyrrole-2-carboxamido)pyrrole-2-carboxamido)pyrazole-5-carboxamido)pyrazole-5-carboxamido)propionamidine;

53) β-(1-methyl-3-(1-methyl-4-(1-methyl-3-(α-bromoacrylamido)pyrazole-5-carboxamido)pyrrole-2-carboxamido)pyrazole-5-carboxamido)propionamidine;

54) β-(1-methyl-3-(1-methyl-4-(1-methyl-4-(α-bromoacrylamido)imidazole-2-carboxamido)pyrrole-2-carboxamido)pyrazole-5-carboxamido)propionamidine;

55) β-(1-methyl-3-(1-methyl-4-(1-methyl-4-(1-methyl-3-(α-bromoacrylamido)pyrazole-5-carboxamido)pyrrole-2-carboxamido)pyrrole-2-carboxamido)pyrazole-5-carboxamido)propionamidine;

56) β-(1-methyl-3-(1-methyl-4-(1-methyl-4-(1-methyl-4-(α-bromoacrylamido)imidazole-2-carboxamido)pyrrole-2-carboxamido)pyrrole-2-carboxamido)pyrazole-5-carboxamido)propionamidine;

57) β-(1-methyl-3-(1-methyl-4-(1-methyl-4-(3-(α-bromoacrylamido)1,2,4,triazole-5-carboxamido)pyrrole-2-carboxamido)pyrrole-2-carboxamido)pyrazole-5-carboxamido)propionamidine;

58) β-(1-methyl-3-(1-methyl-4-(1-methyl-4-(1-methyl-4-(α-bromoacrylamido)pyrrole-2-carboxamido)pyrrole-2-carboxamido)pyrrole-2-carboxamido)pyrazole-5-carboxamido)propionamidine;

59) β-(1-methyl-3-(1-methyl-4-(1-methyl-3-(1-methyl-3-(α-bromoacrylamido)pyrazole-5-carboxamido)pyrazole-5-carboxamido)pyrrole-2-carboxamido)pyrazole-5-carboxamido)propionamidine;

60) β-(1-methyl-3-(1-methyl-4-(1-methyl-3-(1-methyl-4-(α-bromoacrylamido)pyrrole-2-carboxamido)pyrazole-5-carboxamido)pyrrole-2-carboxamido)pyrazole-5-carboxamido)propionamidine;

61) β-[1-methyl-4-[1-methyl-4-[1-methyl-4-[2-[4-N,N-bis(2-chloroethyl)amino-benzene-1-carboxamido]thiazole-4-carboxamido]pyrrole-2-carboxamido]pyrrole-2-carboxamido]pyrrole-2-carboxamido]propionamidine;

62) β-[1-methyl-4-[1-methyl-4-[1-methyl-4-[1-methyl-4-[4-N,N-bis(2-chloroethyl)amino-benzene-1-carboxamido]imidazole-2-carboxamido]pyrrole-2-carboxamido]pyrrole-2-carboxamido]pyrrole-2-carboxamido]propionamidine;

63) β-[1-methyl-4-[1-methyl-4-[1-methyl-4-[3-[4-N,N-bis(2-chloroethyl)amino-benzene-1 carboxamido]1,2,4,triazole-5-carboxamido]pyrrole-2-carboxamido]pyrrole-2-carboxamido]pyrrole-2-carboxamido]propionamidine;

64) β-[1-methyl-3-[1-methyl-3-[2-[4-N,N-bis(2-chloroethyl)amino-benzene-1-carboxamido]thiazole-4-carboxamido]pyrazole-5-carboxamido]pyrazole-5-carboxamido]propionamidine;

65) β-[1-methyl-4-[1-methyl-4-[1-methyl-3-[1-methyl-4-[4-N,N-bis(2-chloroethyl)amino-benzene-1-carboxamido]imidazole-2-carboxamido]pyrazole-5-carboxamido]pyrrole-2-carboxamido]pyrrole-2-carboxamido]propionamidine;

66) β-[1-methyl-4-[1-methyl-4-[1-methyl-3-[1-methyl-4-[4-N,N-bis(2-chloroethyl)amino-benzene-1-carboxamido]pyrrole-2-carboxamido]pyrazole-5-carboxamido]pyrrole-2-carboxamido]pyrrole-2-carboxamido]propionamidine;

67) β-[1-methyl-4-[1-methyl-3-[1-methyl-3-[4-N,N-bis(2-chloroethyl)amino-benzene-1-carboxamido]pyrazole-5-carboxamido]pyrazole-5-carboxamido]pyrrole-2-carboxamido]propionamidine;

68) β-[1-methyl-4-[1-methyl-3-[1-methyl-4-[4-N,N-bis(2-chloroethyl)amino-benzene-1-carboxamido]pyrrole-2-carboxamido]pyrazole-5-carboxamido]pyrrole-2-carboxamido]propionamidine;

69) β-(1-methyl-4-(1-methyl-3-(1-methyl-4-(α-bromoacrylamido)pyrrole-2-carboxamido)pyrazole-5-carboxamido)pyrrole-2-carboxamido)propionamidine;

70) β-(1-methyl-4-(1-methyl-3-(1-methyl-3-(α-bromoacrylamido)pyrazole-5-carboxamido)pyrazole-5-carboxamido)pyrrole-2-carboxamido)propionamidine;

71) β-(1-methyl-4-(1-methyl-4-(1-methyl-3-(1-methyl-4-(α-bromoacrylamido)pyrrole-2-carboxamido)pyrazole-5-carboxamido)pyrrole-2-carboxamido)pyrrole-2-carboxamido)propionamidine;

72) β-(1-methyl-4-(1-methyl-4-(1-methyl-3-(1-methyl-4-(α-bromoacrylamido)imidazole-2-carboxamido)pyrazole-5-carboxamido)pyrrole-2-carboxamido)pyrrole-2-carboxamido)propionamidine;

73) β-[1-methyl-4-[1-methyl-4-[1-methyl-3-[4-N,N-bis(2-bromoethyl)amino-benzene-1-carboxamido]

pyrazole-5-carboxamido]pyrrole-2-carboxamido] pyrrole-2-carboxamido]propionamidine;

74) β-[1-methyl-3-[1-methyl-4-[1-methyl-4-[4-N,N-bis (2-bromoethyl)amino-benzene-1-carboxamido] pyrrole-2-carboxamido]pyrrole-2-carboxamido] pyrazole-5-carboxamido]propionamidine;

75) β-[1-methyl-3-[1-methyl-3-[1-methyl-4-[4-N,N-bis (2-bromoethyl)amino-benzene-1-carboxamido] pyrrole-2-carboxamido]pyrazole-5-carboxamido] pyrazole-5-carboxamido]propionamidine;

76) β-[1-methyl-4-[1-methyl-4-[1-methyl-4-[1-methyl-3-[4-N,N-bis(2-bromoethyl)amino-benzene-1-carboxamido]pyrazole-5-carboxamido]pyrrole-2-carboxamido]pyrrole-2-carboxamido]propionamidine; 77) β-[1-methyl-3-[1-methyl-3-[1-methyl-4-[1-methyl-3-(4-N,N-bis(2-bromoethyl)amino-benzene-1-carboxamido]pyrazole-5-carboxamido]pyrrole-2-carboxamido]pyrazole-5-carboxamido]pyrazole-5-carboxamido]propionamidine;

78) β-[1-methyl-3-[1-methyl-3-[1-methyl-4-[1-methyl-4-[4-N,N-bis(2-bromoethyl)amino-benzene-1-carboxamido]pyrrole-2-carboxamido]pyrrole-2-carboxamido]pyrazole-5-carboxamido]propionamidine;

79) β-[1-methyl-3-[1-methyl-4-[1-methyl-4-(1-methyl-3-[4-N,N-bis(2-bromoethyl)amino-benzene-1-carboxamido]pyrazole-5-carboxamido]pyrrole-2-carboxamido]pyrrole-2-carboxamido]pyrazole-5-carboxamido]propionamidine;

80) β-[1-methyl-3-[1-methyl-4-[1-methyl-4-[1-methyl-4-[4-N,N-bis(2-bromoethyl)amino-benzene-1-carboxamido]pyrrole-2-carboxamido]pyrrole-2-carboxamido]pyrrole-2-carboxamido]pyrazole-5-carboxamido]propionamidine;

81) β-[1-methyl-3-[1-methyl-4-[1-methyl-3-[1-methyl-4-[4-N,N-bis(2-bromoethyl)amino-benzene-1-carboxamido]pyrrole-2-carboxamido]pyrazole-5-carboxamido]pyrrole-2-carboxamido]pyrazole-5-carboxamido]propionamidine, and the pharmaceutically acceptable salts thereof, especially the salts with hydrochloric acid or hydrobromic acid.

The compounds of formula (I) or a pharmaceutically acceptable salt thereof are prepared by a process comprising:

a) reacting a compound of formula (II)

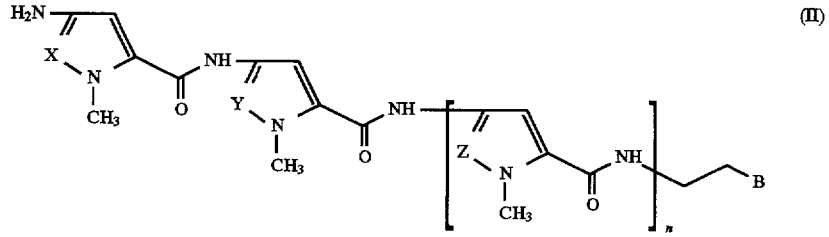

wherein X, Y, Z, B and n are as defined above or a salt thereof with a compound of formula (III)

wherein $R_1$, $R_2$ and A are as defined above and W is hydroxy or a leaving group; or b) reacting a compound of formula (IV)

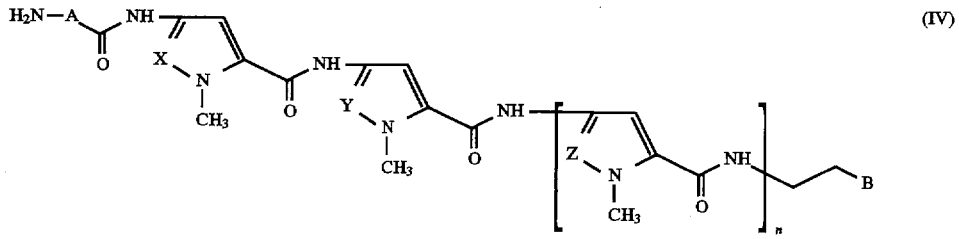

wherein A, X, Y, Z, B and n are as defined above or a salt thereof with a compound of formula (V)

wherein $R_1$ and W are as defined above so obtaining a compound of formula (I) wherein $R_1$ is as defined above and $R_2$ is hydrogen or is the same as $R_1$ and, if desired, salifying a compound of formula (I) or obtaining a free compound from a salt, and/or, if desired, separating a mixture of isomers of formula (I) into the single isomers.

The leaving group W in the compounds (III) and (V) may be, for example, halogen, in particular chlorine, or another displaceable group such as, for instance 2,4,5-trichlorophenoxy, 2,4-dinitrophenoxy, succinamido-N-oxy, imidazolyl, pivaloyloxy

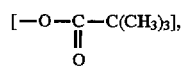

ethyloxy formate

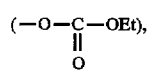

isopropyloxyformate

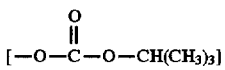

or α-bromoacryloxy

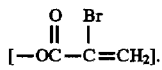

The reaction between a compound of formula (II), according to the process variant a), and a compound of formula (III) wherein W is OH, is preferably carried out in a molar ratio ranging from about 1:1 to about 1:2 in an organic solvent such as, e.g., dimethylsulphoxide, hexamethylphosphotriamide, dimethylacetamide, dioxane, or, preferably, dimethylformamide, or their aqueous mixtures, in the presence of an organic base such as, e.g., triethylamine or N,N'-diisopropylethylamine or an inorganic base such as, e.g., sodium bicarbonate and in the presence of a condensing agent such as, e.g., N,N'-dicyclohexylcarbodiimide, or preferably 1-ethyl-3-(3'-dimethylaminopropyl)carbodiimide hydrochloride.

The reaction temperature may vary from about −10° C. to about 50° C. and the reaction time from about 1 to about 24 hours.

The reaction between a compound of formula (II) and a compound of formula (III), wherein W is a leaving group, as defined above, according to the process step a), may be carried out at a molar ratio ranging from about 1:1 to about 1:2 in an organic solvent such as, e.g., dimethylformamide, dioxane, pyridine, tetrahydrofurane or their aqueous mixture in the presence of an organic base, e.g. N,N'diisopropylethylamine, triethylamine, or an inorganic base, e.g. sodium bicarbonate, at a temperature from about 0° C. to about 100° C. and for a time varying from about 2 hours to about 48 hours.

The reaction between a compound of formula (IV) and a compound of formula (V), according to the process variant b), may be carried out in analogous conditions as reported hereinabove for the process variant a).

When W in the compounds of formula (V) is a leaving group, it is preferably chlorine.

When $R_1$ and $R_2$ have the same meaning, the reaction is carried out in a molar ratio, between (V) and (IV), from about 2:1 to about 3:1 in an organic solvent or their aqueous mixtures in presence of an organic or inorganic base as reported hereinabove. The salification of a compound of formula (I) as well as the preparation of a free compound from a salt and the separation of a mixture of isomers into the single isomers may be carried out by known standard methods.

The compounds of formula (I) prepared according to the above described procedures may be purified by conventional methods such as, e.g., H.P.L.C. silica gel or alumina column chromatography, and/or by recrystallization from an organic solvent such as, e.g., a lower aliphatic alcohol, e.g. methyl, ethyl, propyl, isopropyl alcohol or dimethylformamide.

The compounds of formulae (III) and (V) are known compounds or may be prepared by standard methods from known compounds, as described for example in J.O.C. 26, 4996 (1961); J.A.C.S. 62, 3495 (1940); J. Med. Chem. 9, 882 (1966), 25, 178 (1982), 21, 16 (1978) and 8, 167 (1965).

The compounds of formula (IV) may be prepared from compounds of formula (VI)

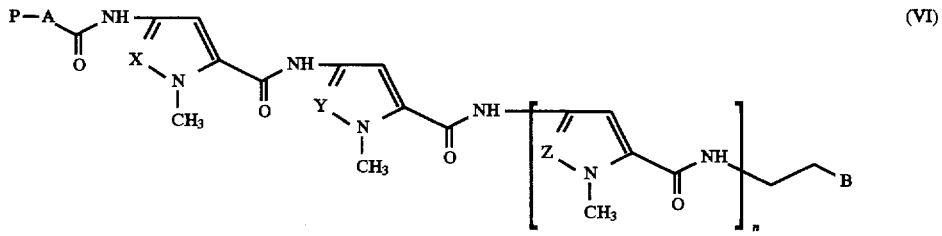

wherein P is a nitro group or an amino group appropriately protected with a group such as t-butyloxycarbonyl

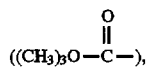

triphenylmethyl [(Ph)$_3$C—] or preferably carbobenzyloxy,

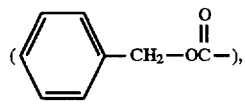

and A, X, Y, Z, n, B are as defined above.

The conversion of the nitro group into an amino group may be carried out according to known procedures using for instance a solvent such as dioxane, methanol, ethanol or their aqueous mixture at room temperature and under 50 psi pressure of hydrogen in the presence of 10% Palladium on charcoal.

The conversion of protected amine into the free amine may be carried out according to known procedures.

See for example J. Org. Chem. 43, 2285, (1978) when the protecting group is t-butyloxycarbonyl; J. Org. Chem. 44, 811 (1979); J. Am. Chem. Soc. 78, 1359 (1956) when the protecting group is triphenylmethyl or Ber. 65, 1192 (1932) when the protecting group is carbobenzyloxy.

The compounds of formula (VI) may be prepared by a process comprising reacting a compound of formula (II) with a compound of formula (VII)

wherein A, W and P are as defined above, W being preferably chlorine or OH.

The reaction conditions are the same as reported above for the process variant (a).

The compounds of formula (VII) are known or may be prepared by known methods. See for example: Acta. Chem. Scan. 44, 75 (1990); Tetrahedron 44, 5833 (1988); J. Org. Chem. 50, 3774 (1985) and 52, 3493 (1987); Heterocycles 31, 1629 (1990).

The compounds of formula (II) may be prepared from compounds of formula (VIII)

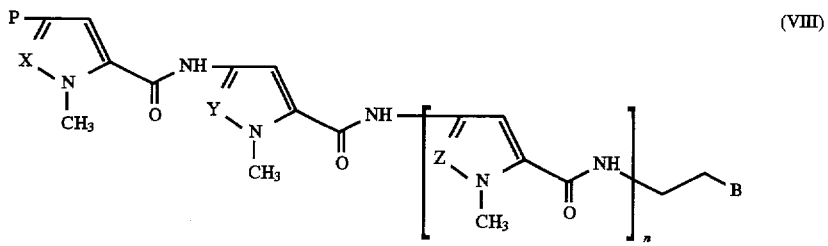

(VIII)

wherein P, X, Y, Z, n and B are as defined above and the reaction conditions for transformation of the P group into amino group are the same as reported above for the conversion of the compounds of formula (VI) into the compounds of formula (IV).

The compounds of formula (VIII) may be prepared by different methods depending on the meaning of P and B.

The compounds of formula (VIII), wherein X, Y, Z and n are as defined above, P is a nitro group and B is

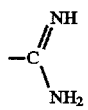

may be prepared from compounds of formula (IX)

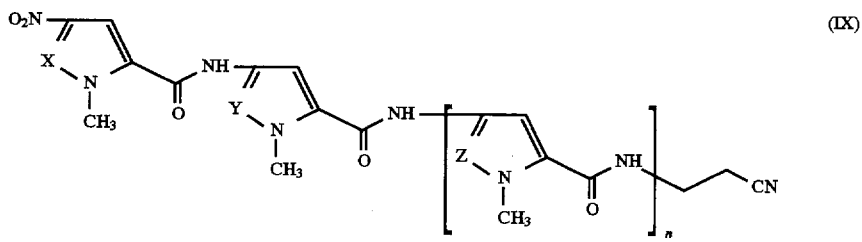

wherein X, Y, Z and n are as defined above.

The conversion of the nitrile group into the amidine may be carried out using Pinner Synthesis as reported in Ann. Chim. (Paris) 14, 5, 23–27 (1970).

The compounds of formula (VIII), wherein X, Y, Z and n are as defined above, P is a nitro group and B is a group

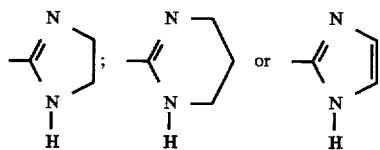

may be obtained from the compounds of formula (VIII) wherein X, Y, Z and n are as defined above, P is a nitro group and B is

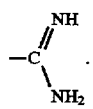

The conversion of the amidino group into the 2-imidazole ring may be, e.g., carried out by reaction with, e.g., aminoacetaldehydedimethylacetal according to known procedure, while ethylenediamine may be used for converting the amidino into the 2-imidazoline group; the conversions into the other heterocycles may be carried out in similar way by known methods.

The compounds of formula (IX) may be prepared by a process comprising reacting a compound of formula (X)

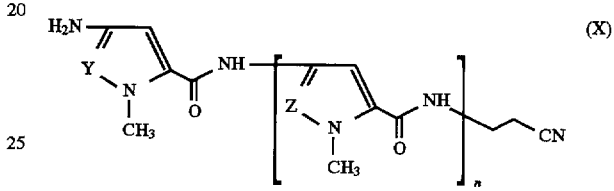

(X)

wherein Y, Z and n are as defined above with compounds of formula (XI)

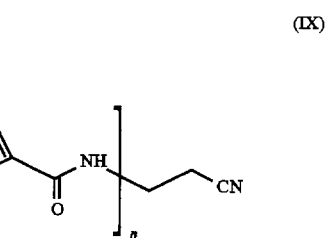

(XI)

wherein X is as defined above and G is a leaving group such as chlorine and imidazolyl or an OH group. The reaction conditions are the same reported in the process steps (a).

The compounds of formula (XI) wherein X is CH are known or may be prepared by standard methods, see J. Med. Chem. 26, 1042–1049 (1983).

The compound of formula (XI) wherein X is N may be prepared from compounds of formula (XII)

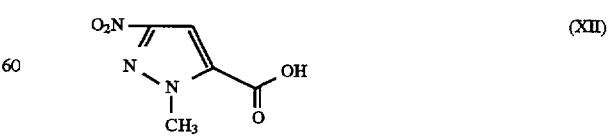

(XII)

The reaction may be carried out according to known procedure using, for instance, when G is chlorine, $SOCl_2$ in an inert solvent such as dioxane, benzene, at reflux temperature for a time from about 0.5 to about 2 hours; when G is imidazolyl, carbonyldiimidazole can be used and a solvent such as benzene, ethyl acetate, dioxane or dimethylformamide.

The compounds of formula (XII) may be prepared from compounds of formula (XIII)

O₂N—⟨pyrazole-N-CH₃⟩—CH=CH—C(=O)—O—L   (XIII)

wherein L is an alkyl group such as methyl or ethyl.

The reaction may be carried out by hydrolytic condition according to known procedures using for instance NaOH, KOH in an organic solvent such as dioxane or acetonitrile, at room temperature for a time from about 1 to about 24 hours.

The compound of formula (XIII) may be prepared from a compound of formula (XIV)

H₂N—⟨pyrazole-N-CH₃⟩—CH=CH—C(=O)—O—L   (XIV)

wherein L is as defined above, by oxidation.

The reaction may be carried out using from about 3 equivalents to about 5 equivalents of 3-chloroperbenzoic acid in an organic solvent such as chloroform, dioxane or acetonitrile at a temperature from about 50° C. to about 80° C. and for a time from about 1 to about 5 hours.

The compounds of formula (XIV) are known or may be prepared by known methods, see for example Acta Chem. Scan. 44, 75 (1990) or J. Org. Chem. 54, 431–434 (1989).

The compounds of formula (X), wherein n is 0 or 1 and Y=Z=CH, are known, see for example J. Med. Chem. 26, 1042–1049 (1983) and J. Org. Chem. 50, 3774 (1985) and 52, 3493 (1987).

The compounds of formula (X), wherein n is 0 or 1 and Y and Z are N, may be prepared by known methods, see for example Anti-Cancer Drug Des. 6, 501–517 (1991).

The compounds of formula (X) wherein n is 1 and one of Y and Z is N and the other is CH, may be prepared reacting a compound of formula (XV)

P—⟨pyrazole-Y-N-CH₃⟩—CH=CH—C(=O)—G   (XV)

wherein P, Y, G are as defined above with a compound of formula (XVI)

H₂N—⟨pyrazole-Z-N-CH₃⟩—CH=CH—C(=O)—NH—CH₂CH₂—CN   (XVI)

The reaction may be carried out in the same condition as reported in the process step (a).

The compounds of formula (XV) are known or may be prepared by known methods, for example, when P is NO₂ and Y is N the reaction may be carried out as reported above for the compound (XI).

The compounds of formula (XVI) are known compounds (J. Org. Chem. 50, 3774 (1985) and 52,3493 (1987); Anti-Cancer Drug Des. 6, 501–517 (1991)).

The compounds of formula (VIII) wherein P is an amino group protected as terbutyloxycarbonyl (Boc), triphenylmethyl or, preferably, carbobenzyloxy (Cbz), and X, Y, Z, n, B are as defined above, may be prepared by a process comprising reacting a compound of formula (XVII)

T—NH—⟨pyrazole-X-N-CH₃⟩—CH=CH—C(=O)—G   (XVII)

wherein T is a protecting group of the amino group, preferably carbobenzyloxy, and G is as defined above, with a compound of formula (XVIII)

H₂N—⟨pyrazole-Y-N-CH₃⟩—C(=O)—NH—[⟨pyrazole-Z-N-CH₃⟩—C(=O)—NH—]ₙ—B   (XVIII)

wherein Y, Z, n and B are as defined above.

The reaction conditions are the same as reported in the process steps (a).

The compounds of formula (XVII) are known or may be prepared by known methods, see for example Acta Chem. Scan. 44, 75–81 (1990) and J. Med. Chem. 26, 1042–1049 (1983).

The compounds of formula (XVIII) may be prepared by reducing compounds of formula (XIX)

O₂N—⟨pyrazole-Y-N-CH₃⟩—C(=O)—NH—[⟨pyrazole-Z-N-CH₃⟩—C(=O)—NH—]ₙ—B   (XIX)

wherein Y, Z, n and B are as defined above.

The reduction may be carried out by catalytic hydrogenation according to known procedures.

The compound of formula (XIX), wherein B is

—C(=NH)—NH₂ and Y, Z, n are as defined above, may be prepared from compounds of formula (XX)

O₂N—⟨pyrazole-Y-N-CH₃⟩—C(=O)—NH—[⟨pyrazole-Z-N-CH₃⟩—C(=O)—NH—]ₙ—CH₂CH₂—CN   (XX)

wherein Y, Z and n are as defined above.

The conversion of the nitrile group into the amidine may be carried out using Pinner synthesis as reported in Ann. Chim. (Paris) 14, 5, 23–27 (1970).

The compounds of formula (IX) wherein B is a group

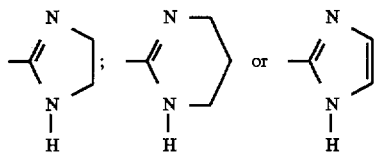

and Y, Z, n are as defined above, may be prepared from amidine derivatives using procedure as reported above for the corresponding compounds of formula (VIII).

The compounds of formula (XX) wherein n is as defined above and each of Y and Z is —CH— are known compounds, see for example J. Org. Chem. 50, 3774 (1985) and 52, 3493 (1987).

The compounds of formula (XX) wherein n is 0 and Y is N may be prepared by a process comprising reacting a compound of formula (XII) as defined above with 3-amino propionitrile.

The reaction may be carried out according to known procedures, see for example Anti-Cancer Drug Des. 6, 501–517 (1991).

The compounds of formula (XX), wherein n is 1 and Y and Z are as defined above but not both CH, may be prepared by a process comprising reacting a compound of formula (XI), wherein X is N or CH and G is as defined above, with a compound of formula (XVI) as defined above.

The reaction conditions are the same as reported above in the process step (a).

The compounds of the invention show cytotoxic properties towards tumor cells so that they can be useful as antineoplastic agents, e.g. to inhibit the growth of various tumors such as, for instance, carcinomas, e.g. mammary carcinoma, lung carcinoma, bladder carcinoma, colon carcinoma, ovary and endometrial tumors. Other neoplasias in which the compounds of the invention could find application are, for instance, sarcomas, e.g. soft tissue and bone sarcomas, and the hematological malignancies such as, e.g., leukemias.

The antitumor activity was evaluated in vitro by cytotoxicity studies carried out on murine L1210 leukemia cell. Cells were derived from in vivo tumors and established in cell culture. Cells were used until the tenth passage. Cytotoxicity was determined by counting surviving cells after 4 hours treatment and 48 hours growth in drug-free medium.

The percentage of cell growth in the treated cultures was compared with that of controls. $ID_{50}$ values (doses inhibiting 50% of the cellular growth in respect to controls) were calculated on dose-response curves.

Thus, for example, the compound β-[1-methyl-3-[1-methyl-3-[1-methyl-4-[4-N,N-bis(2-chloroethyl)amino-benzene-1-carboxamido]pyrrole-2-carboxamido]pyrazole-5-carboxamido]pyrazole-5-carboxamido]propionamidine hydrochloride showed an $ID_{50}$ of 0.5 μg/ml.

The compounds of the invention were tested also in vivo on murine $L_{1210}$ leukemia and on murine reticulosarcoma M 5076, showing a very good antitumoral activity, with the following procedure.

$L_{1210}$ murine leukemia was maintained in vivo by i.p. serial transplantation. For experiments, $10^5$ cells were injected i.p. in CD2F1 female mice, obtained from Charles River Italy. Animals were 8 to 10 weeks old at the beginning of the experiments. Compounds were administered i.p. at day +1 after tumor cells injections.

M5076 reticulosarcoma was maintained in vivo by i.m. serial transplantation. For experiments, $5 \times 10^5$ cells were injected i.m. in C57B16 female mice, obtained from Charles River Italy. Animals were 8 to 10 weeks old at the beginning of the experiments. Compounds were administered i.v. at day 3, 7 and 11 after tumor injection.

Survival time of mice and tumor growth were calculated and activity was expressed in term of T/C % and T.I. %.

$$T/C = \frac{\text{median survival time treated group}}{\text{median survival time untreated group}} \times 100$$

T.I.=% inhibition of tumor growth respect to control
Tox: number of mice which died for toxicity.

Tox determination was made when mice died before the control and/or tested significant body weight loss and/or spleen and/or liver size reduction were observed.

The compounds of the invention showed a high antitumor activity in these tumor models.

For example, the compound β-[1-methyl-3-[1-methyl-3-[1-methyl-4-[4-N,N-bis(2-chloroethyl)amino-benzene-1-carboxamido]pyrrole-2-carboxamido]pyrazole-5-carboxamido]pyrazole-5-carboxamido]propionamidine hydrochloride (FCE 28164) was tested against intraperitoneal $L_{1210}$ murine leukemia showing the activity reported in the table below.

|  | mg/kg | T/C % | Tox |
|---|---|---|---|
| Compound FCE 28164 | 25 | 259 | 0/10 |

The compounds of the invention can also be useful as antiviral agents.

The compounds of the invention can be administered by the usual routes, for example, parenterally, e.g. by intravenous injection or infusion, intramuscularly, subcutaneously, topically or orally.

The dosage depends on the age, weight and conditions of the patient and on the administration route.

For example, a suitable dosage for administration to adult humans may range from about 0.05 to about 100 mg pro dose 1–4 times a day.

The pharmaceutical compositions of the invention contain a compound of formula (I) as the active substance, in association with one or more pharmaceutically acceptable excipients.

The pharmaceutical compositions of the invention are usually prepared following conventional methods and are for administered in a pharmaceutically suitable form.

For instance, solutions for intravenous injection or infusion may contain as carrier, for example, sterile water or preferably, they may be in the form of sterile aqueous isotonic saline solutions.

Suspensions or solutions for intramuscular injections may contain, together with the active compound a pharmaceutically acceptable carrier, e.g. sterile water, olive oil, ethyl oleate, glycols, e.g. propylene glycol, and if desired, a suitable amount of lidocaine hydrochloride.

In the form for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl-cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or film-coating processes.

Furthermore, according to the invention there is provided a method of treating viral infections and tumors in a patient in need of it, comprising administering to the said patient a composition of the invention.

The following examples illustrate but do not limit the invention.

The abbreviations DMF and THF stand, respectively, for dimethylformamide and tetrahydrofurane.

EXAMPLE 1

β-[1-methyl-4-[1-methyl-4-[1-methyl-3-[4-N,N-bis (2-chloroethyl)amino-benzene-1-carboxamido] pyrazole-5-carboxamido]pyrrole-2-carboxamido] pyrrole-2-carboxamido]propionamidine, hydrochloride (Compound no. 1)

Step one—Synthesis of the intermediate 1-methyl-3-[4-N, N-bis(2-chloroethyl)amino-benzene-1-carboxamido] pyrazole-5-carboxilic acid.

To a solution containing 0.84 g of methyl 1-methyl-3-aminopyrazole-5-carboxylate in 20 ml of dioxane (prepared as in J. Org. Chem. 54, 431–434, 1989) and 0.76 ml of triethylamine, 1.42 g of 4-N,N-bis(2-chloroethyl) aminobenzoyl chloride (prepared as in J. Org. Chem. 26, 4996–4997, 1961) were added. The mixture was stirred overnight, concentrated to small volume, diluted with 30 ml of 5% hydrochloric acid and extracted with ethyl acetate. The organic phase was dried over anhydrous sodium sulphate, after evaporation of the solvent a solid residue was obtained which was purified by recrystallization from diethyl ether to yield 1.64 g of methyl 1-methyl-3-[4-N,N-bis(2-chloroethyl)amino-benzene-1-carboxamido]pyrazole-5-carboxylate.

The derivative obtained (1.64 g) was dissolved in 15 ml of dioxane and added of 4.1 ml of 2N potassium hydroxide.

The mixture was stirred for two hours, concentrated to small volume, acidified with 10% hydrochloric acid and extracted with ethyl acetate. The organic phase was dried over anhydrous sodium sulphate, the solvent evaporated in vacuo and the solid residue purified by recrystallization from ethyl acetate-hexane yielding 1.07 g of the intermediate.

m.p. 129°–130° C.

PMR(DMSO-$d_6$) δ: 13.25 (b.s.,1H), 10.68 (s,1H), 7.92 (d,J=8.7 Hz,2H), 7.13 (s,1H), 6.82 (d,J=8.7 Hz,2H), 4.03 (s,3H), 3.78 (m,4H), 2.50 (m,4H)

By analogous procedure the following compounds can be prepared:

2-[4-N,N-bis(2-chloroethyl)amino-benzene-1-carboxamido]thiazole-4-carboxylic acid m.p.270°–275° C. dec.

PMR(DMSO-$d_6$) δ: 12.82 (b.s.,1H), 12.64 (b.s.,1H), 8.04 (d,J=8.7 Hz,2H), 7.98 (s,1H), 6.88 (d,J=8.7 Hz,2H), 3.79 (m,8H)

3-[4-N,N-bis(2-chloroethyl)amino-benzene-1-carboxamido]1,2,4,triazole-5-carboxylic acid; 1-methyl-4-[4-N,N-bis(2-chloroethyl)amino-benzene-1-carboxamido]pyrrole-2-carboxylic acid m.p. 155°–157° C.

PMR(DMSO-$d_6$) δ: 11.75 (b.s.,1H), 9.91 (s,1H), 7.81 (d,J=8.7 Hz,1H), 7.28 (d,J=1.7 Hz,1H), 6.88 (d,J=8.7 Hz,1H), 6.64 (d,J=1.7 Hz,1H), 3.83 (s,1H), 3.35 (m,8H)

1-methyl-4-[4-N,N-bis(2-chloroethyl)amino-benzene-1-carboxamido]imidazole-2-carboxylic acid Step two—The title compound To a solution of 0.25 g of intermediate in 20 ml of dry dimethylformamide was added 0.24 g of β-[1-methyl-4-[1-methyl-4-aminopyrrole-2-carboxamido]pyrrole-2-carboxamido]propionamidine, dihydrochloride (prepared as in J. Med. Chem.32, 774–778,1989), 0.13 ml of N,N'-diisopropylethylamine and 0.17 g of 1-ethyl-3-(3'-dimethylaminopropyl)carbodiimide hydrochloride.

The mixture was stirred overnight at room temperature and brought to pH 4–5 with 10% hydrochloric acid. After evaporation of the solvent a solid residue was obtained which was purified by HPLC using as eluant a mixture of acetonitrile-water-trifluoroacetic acid (10–90–0.1), yielding 0.204 g of the title compound.

FAB-MS: m/z 698,(41,[M+H]$^+$); 244 (100)

m.p. 210°–215° C.

PMR(DMSO-$d_6$) δ: 10.65 (s,1H), 10.47 (s,1H), 9.98 (s,1H), 9.0 (b.s.,2H), 8.6 (b.s.,2H), 8.22 (m,1H), 7.93 (m,2H), 7.45 (s,1H), 7.30 (d,J=1.7 Hz,1H), 7.19 (d,J=1.7 Hz,1H), 7.09 (d,J=1.7 Hz,1H), 6.94 (d,J=1.7 Hz,1H), 6.8 (m,2H), 4.04 (s,3H), 3.85 (s,3H), 3.8 (s,3H), 3.6–3.9 (m,8H), 3.49 (m,2H), 2.6 (m,2H)

By analogous procedure and using the opportune starting material the following compounds can be prepared:

β-[1-methyl-4-[1-methyl-4-[2-[4-N,N-bis(2-chloroethyl) amino-benzene-1-carboxamido]thiazole-4-carboxamido] pyrrole-2-carboxamido]pyrrole-2-carboxamido] propionamidine,hydrochloride (Compound no. 2)

FAB-MS: m/z 701,(60,[M+H]$^+$)

m.p. 230°–233° C.

PMR(DMSO-$d_6$) δ: 9.91 (s,1H), 9.78 (s,1H), 8.87 (b.s., 2H), 8.55 (b.s.,2H), 8.19 (m,1H), 8.02 (m,2H), 7.83 (b.s., 1H), 7.28 (d,J=1.7 Hz,1H), 7.18 (d,J=1.7 Hz,1H), 7.09 (d,J=1.7 Hz,1H), 6.94 (d,J=1.7 Hz,1H), 6.86 (m,2H), 3.7–3.9 (m,8H), 3.86 (s,3H), 3.81 (s,3H), 3.50 (m,2H), 2.61 (m,2H)

β-[1-methyl-4-[1-methyl-4-[1-methyl-4[4-N,N-bis(2-chloroethyl)amino-benzene-1-carboxamido]imidazole-2-carboxamido]pyrrole-2-carboxamido]pyrrole-2-carboxamido]propionamidine,hydrochloride (Compound no. 8);

β-[1-methyl-4-[1-methyl-4-[3-[4-N,N-bis(2-chloroethyl) amino-benzene-1-carboxamido]1,2,4,triazole-5-carboxamido]pyrrole-2-carboxamido]pyrrole-2-carboxamido]propionamidine,hydrochloride (Compound no. 6);

β-[1-methyl-4-[1-methyl-4-[1-methyl-3-[4-N,N-bis(2-bromoethyl)amino-benzene-1-carboxamido]pyrazole-5-carboxamido]pyrrole-2-carboxamido]pyrrole-2-carboxamido]propionamidine hydrobromide (Compound no. 73);

β-[1-methyl-3-[1-methyl-3-[1-methyl-4-[1-methyl-3-[4-N, N-bis(2-bromoethyl)amino-benzene-1-carboxamido] pyrazole-5-carboxamido]pyrrole-2-carboxamido] pyrazole-5-carboxamido]pyrazole-5-carboxamido] propionamidine hydrobromide (Compound no. 77);

β-[1-methyl-3-[1-methyl-3-[1-methyl-4-[1-methyl-4-[4-N, N-bis(2-bromoethyl)amino-benzene-1-carboxamido] pyrrole-2-carboxamido]pyrrole-2-carboxamido]pyrazole-5-carboxamido]pyrazole-5-carboxamido]propionamidine hydrobromide (Compound no. 78).

EXAMPLE 2

β-[1-methyl-4-[1-methyl-4-[1-methyl-4-[1-methyl-3-[4-N,N-bis(2-chloroethyl)amino-benzene-1-carboxamido]pyrazole-5-carboxamido]pyrrole-2-carboxamido]pyrrole-2-carboxamido]pyrrole-2-carboxamido]propionamidine, hydrochloride
(Compound no. 13)

To a solution containing 0.3 g of N-deformyl distamycin A dihydrochloride (prepared as in J. Med. Chem. 32, 774–778, 1989) and 0.23 g of 1-methyl-3-[4-N,N-bis(2-chloroethyl)amino-benzene-1-carboxamido]pyrazole-5-carboxylic acid (prepared as reported in step one of Example 1) in 10 ml of dry dimethylformamide was added 0.17 g of 1-ethyl-3-(3'-dimethylaminopropyl)carbodiimide hydrochloride and 0.1 ml of N,N'-diisopropylethylamine.

The solution was stirred at room temperature overnight, the solvent evaporated in vacuo and the solid residue purified by HPLC using as eluant a mixture of acetonitrile-water-trifluoroacetic acid (10-90-0.1), yielding 0.25 g of the title compound.

FAB-MS: m/z 820,(20,[M+H]$^+$)

U.V. (EtOH 95%): λ max 312.85, ε=67791

PMR(DMSO-d$_6$) δ: 10.65 (b.s.,1H), 10.47 (b.s.,1H), 10.01 (s,1H), 9.93 (s,1H), 8.8 (b.s.,4H), 8.22 (m,1H), 7.93 (m,2H), 7.46 (s,1H), 7.31 (d,J=1.8 Hz,1H), 7.24 (d,J=1.8 Hz,1H), 7.18 (d,J=1.8 Hz,1H), 7.11 (d,J=1.8 Hz,1H), 7.06 (d,J=1.8 Hz,1H), 6.94 (d,J=1.8 Hz,1H), 6.81 (m,2H), 4.05 (s,3H), 3.6–3.9 (m,8H), 3.86 (s,3H), 3.84 (s,3H), 3.8 (s,3H), 3.48 (m,2H), 2.59 (m,2H)

By analogous procedure and using the opportune starting material the following compounds can be prepared:

β-[1-methyl-4-[1-methyl-4-[1-methyl-4-[2-[4-N,N-bis(2-chloroethyl)amino-benzene-1-carboxamido]thiazole-4-carboxamido]pyrrole-2-carboxamido]pyrrole-2-carboxamido]pyrrole-2-carboxamido]propionamidine, hydrochloride (Compound no. 61);

β-[1-methyl-4-[1-methyl-4-[1-methyl-4-[1-methyl-4-[4-N,N-bis(2-chloroethyl)amino-benzene-1-carboxamido]imidazole-2-carboxamido]pyrrole-2-carboxamido]pyrrole-2-carboxamido]pyrrole-2-carboxamido]propionamidine,hydrochloride (Compound no. 62)
FAB-MS: m/z 820,(10,[M+H]$^+$); 244
U.V. (EtOH 95%): λ max 312.85, ε=67791
PMR(DMSO-d$_6$) δ: 10.41 (s,1H), 9.98 (s,1H), 9.96 (s,1H), 9.91 (s,1H), 8.8 (bs,4H), 8.22 (t,J=6 Hz,1H), 7.9 (m,2H), 7.58 (s,1H), 7.27 (d,J=1.8 Hz,1H), 7.23 (d,J=1.8 Hz,1H), 7.18 (d,J=1.8 Hz,1H), 7.16 (d,J=1.8 Hz,1H), 7.06 (d,J=1.8 Hz,1H), 6.94 (d,J=1.8 Hz,1H), 6.8 (m,2H), 3.98 (s,3H), 3.85 (s,3H), 3.83 (s,3H), 3.8 (s,3H), 3.6–3.9 (m,8H), 3.49 (m,2H), 2.60 (t,J=6.4 Hz,1H).

β-[1-methyl-4-[1-methyl-4-[1-methyl-4-[3-[4-N,N-bis(2-chloroethyl)amino-benzene-1-carboxamido]1,2,4,triazole-5-carboxamido]pyrrole-2-carboxamido]pyrrole-2-carboxamido]pyrrole-2-carboxamido]propionamidine, hydrochloride (Compound no. 63);

β-[1-methyl-4-[1-methyl-4-[1-methyl-4-[1-methyl-3-[4-N,N-bis(2-bromoethyl)amino-benzene-1-carboxamido]pyrazole-5-carboxamido]pyrrole-2-carboxamido]pyrrole-2-carboxamido]pyrrole-2-carboxamido]propionamidine, hydrobromide (Compound no. 76).

EXAMPLE 3

β-[1-methyl-3-[1-methyl-3-[1-methyl-4-[4-N,N-bis(2-chloroethyl)amino-benzene-1-carboxamido]pyrrole-2-carboxamido]pyrazole-5-carboxamido]pyrazole-5-carboxamido]propionamidine, hydrochloride (Compound no. 4)

Step one—Synthesis of the intermediate β-[1-methyl-3-[1-methyl-3-[1-methyl-4-nitropyrrole-2-carboxamido]pyrazole-5-carboxamido]pyrazole-5-carboxamido]propionitrile To a solution containing 1 g of 1-methyl-4-nitropyrrole-2-carboxylic acid (prepared as reported in Tetrahedron 34, 2389, 1978) in 5 ml of dry benzene was added 3 ml of thionyl chloride. The mixture was refluxed for one hour, the solvent evaporated in vacuo, the solid residue was dissolved in 10 ml of dioxane and the solution was added to a solution of 1.86 g of β-[1-methyl-3-[1-methyl-3-aminopyrazole-5-carboxamido]pyrazole-5-carboxamido]propionitrile (prepared as reported in Anti Cancer Drug Des.6,501–517, 1991) and 0.82 ml triethylamine in 10 ml of dioxane.

The mixture was stirred at room temperature overnight, concentrated to small volume, acidified by 10% hydrochloric acid to yield a precipitate which was filtrated and purified by recrystallization from ethyl acetate-dioxane, yielding 1.92 g of intermediate.

m.p. 288°–290° C.

PMR(DMSO-d$_6$) δ11.2 (s,1H), 10.98 (s,1H), 8.99 (b.s., 1H), 8.23 (d,J=1.7 Hz,1H), 7.81 (d,J=1.7 Hz,1H), 7.57 (s,1H), 7.33 (s,1H), 4.06 (s,3H), 4.02 (s,3H), 3.97 (s,3H), 3.45 (t,J=6 Hz,2H), 2.78 (t,J=6 Hz,2H)

By analogous procedure the following compounds can be prepared: β-[1-methyl-3-[1-methyl-3-[1-methyl-4-nitroimidazole-2-carboxamido]pyrazole-5-carboxamido]pyrazole-5-carboxamido]propionitrile;

β-[1-methyl-3-[1-methyl-3-[2-nitrothiazole-4-carboxamido]pyrazole-5-carboxamido]pyrazole-5-carboxamido]propionitrile;

β-[1-methyl-3-[1-methyl-3-[3-nitro-1,2,4,triazole-5-carboxamido]pyrazole-5-carboxamido]pyrazole-5-carboxamido]propionitrile.

Step two—Synthesis of the intermediate β-[1-methyl-3-[1-methyl-3-[1-methyl-4-aminopyrrole-2-carboxamido]pyrazole-5-carboxamido]pyrazole-5-carboxamido]propionamide 0.264 g of intermediate was suspended in anhydrous ethanol and the solution saturated with dry HCl gas. After 24 h at room temperature, the solvent was evaporated in vacuo and the residue treated with ammonia in ethanol. After 24 h at room temperature the solvent was evaporated in vacuo and the solid residue purified by recrystallization from methanol-ethyl acetate to yield 0.23 g of nitro derivative.

The nitro derivative (0.23 g) was dissolved in a mixture of methanol-dioxane-water-5% hydrochloric acid (10:5:5:1) and reduced over Pd catalyst (10% on charcoal) under hydrogen pressure (50 psi) in a Parr apparatus. The solution obtained after filtration of the catalyst was evaporated in vacuo yielding 0.21 gr of intermediate.

By analogous procedure the following compounds can be prepared:

β-[1-methyl-3-[1-methyl-3-[1-methyl-4-aminoimidazole-2-carboxamido]pyrazole-5-carboxamido]pyrazole-5-carboxamido]propionamidine,dihydrochloride;

β-[1-methyl-3-[1-methyl-3-[2-aminothiazole-4-carboxamido]pyrazole-5-carboxamido]pyrazole-5-carboxamido]propionamidine, dihydrochloride;

β-[1-methyl-3-[1-methyl-3-[3-amino-1,2,4,triazole-5-carboxamido]pyrazole-5-carboxamido]pyrazole-5-carboxamido]propionamidine,dihydrochloride.

Step three—The title compound 0.078 g of sodium bicarbonate was added to a solution of 0.21 g of intermediate in 10 ml of mixture dioxane-water (1:1). The mixture was cooled to 0° C. and added in small portions of a solution of 0.174 g of 4-N,N-bis(2-chloroethyl) aminobenzoyl chloride (prepared as reported in J. Org. Chem.26,4996–4997,1961) in 10 ml of dioxane.

The reaction mixture was stirred one hour at room temperature and brought to pH 4–5 with 10% hydrochloric acid.

The solvent was evaporated in vacuo to yield a solid residue which was purified by HPLC using as eluant a mixture of acetonitrile-water-trifluoroacetic acid (10:90:0.1). 0.26 g of the title compound was obtained.

FAB-MS: m/z 699,(40,[M+H]$^+$); 244,(100); 733,(70,[M+ HCl-H]$^-$); 661, (72,[M-HCl-H]$^-$)

m.p. 108°–110° C.

U.V. (EtOH 95%): λ max 309.55 ε=42172; λ max 228.05 ε=31353

PMR(DMSO-d$_6$) δ: 11.12 (s,1H), 10.52 (s,1H), 10.04 (s,1H), 8.79 (t,J=5.8 Hz,1H), 9.0 (b.s.,2H), 8.64 (b.s.,2H), 7.85 (m,2H), 7.52 (s,1H), 7.29 (s,1H), 7.39 (d,J=1.9 Hz,1H), 7.13 (d,J=1.9 Hz,1H), 6.81 (m,2H), 4.03 (s,3H), 4.00 (s,3H), 3.86 (s,3H), 3.6–4.0 (m,8H), 3.53 (m,2H), 2.71 (m,2H).

By analogous procedure the following compounds can be prepared:

β-[1-methyl-3-[1-methyl-3-[1-methyl-4-[4-N,N-bis(2-chloroethyl)amino-benzene-1-carboxamido]imidazole-2-carboxamido]pyrazole-5-carboxamido]pyrazole-5-carboxamido]propionamidine, hydrochloride (Compound no. 11);

β-[1-methyl-3-[1-methyl-3-[2-[4-N,N-bis(2-chloroethyl)amino-benzene-1-carboxamido]thiazole-4-carboxamido]pyrazole-5-carboxamido]pyrazole-5-carboxamido]propionamidine, hydrochloride (Compound no. 64);

β-[1-methyl-3-[1-methyl-3-[3-[4-N,N-bis(2-chloroethyl)amino-benzene-1-carboxamido]1,2,4,triazole-2-carboxamido]pyrazole-5-carboxamido]pyrazole-5-carboxamido]propionamidine, hydrochloride (Compound no. 12);

β-[1-methyl-3-[1-methyl-3-[1-methyl-4-[3-methyl-4-N,N-bis(2-chloroethyl)amino-benzene-1-carboxamido]pyrrole-2-carboxamido]pyrazole-5-carboxamido]pyrazole-5-carboxamido]propionamidine, hydrochloride;

β-[1-methyl-3-[1-methyl-3-[1-methyl-4-[3-methoxy-4-N,N-bis(2-chloroethyl)amino-benzene-1-carboxamido]pyrrole-2-carboxamido)pyrazole-5-carboxamido]pyrazole-5-carboxamido]propionamidine, hydrochloride.

EXAMPLE 4

β-[1-methyl-3-[1-methyl-3-[1-methyl-4-[1-methyl-3-[4-N,N-bis(2-chloroethyl)amino-benzene-1-carboxamido]pyrazole-5-carboxamido]pyrrole-2-carboxamido]pyrazole-5-carboxamido]pyrazole-5-carboxamido]propionamidine,hydrochloride
(Compound no. 14)

To a solution of 0.29 g of 1-methyl-3-[4-N,N-bis(2-chloroethyl)amino-benzene-1-carboxamido]pyrazole-5-carboxylic acid (prepared as in Example 1) in 50 ml of dioxane was added 1 ml of thionyl chloride. The mixture was refluxed for 30 minutes and the solvent was evaporated in vacuo. The solid residue obtained was dissolved in 10 ml of dry dioxane and added slowly to a solution of 0.2 g of β-[1-methyl-3-[1-methyl-3-[1-methyl-4-aminopyrrole-2-carboxamido]pyrazole-5-carboxamido] pyrazole-5-carboxamido]propionamidine,dihydrochloride (prepared as in Example 3) and 0.8 gr of sodium bicarbonate in 20 ml of water. The mixture was stirred at room temperature for two hours and brought to pH 4–5 with 10% hydrochloric acid. After evaporation of solvent a solid residue was obtained which was purified by HPLC using as eluant a mixture of acetonitrile-water-trifluoroacetic acid (10-90-0.1), yielding 0.2 g of the title compound.

FAB-MS: m/z 822,(16,[M+H]$^+$)

m.p. 220°–223° C.

PMR(DMSO-d$_6$) δ: 11.12 (s,1H), 10.64 (s,1H), 10.58 (s,1H), 10.48 (s,1H), 8.78 (t,J=5.8 Hz,1H), 9.0 (b.s.,2H), 8.6 (b.s.,2H), 7.93 (m,2H), 7.53 (s,1H), 7.46 (s,1H), 7.29 (s,1H), 7.40 (d,J=1.8 Hz,1H), 7.18 (d,J=1.8 Hz,1H), 6.81 (m,2H), 4.05 (s,3H), 4.04 (s,3H), 4.01 (s,3H), 3.87 (s,3H), 3.7–3.9 (m,8H), 3.53 (m,2H), 2.61 (m,2H).

By analogous procedure the following compounds can be prepared:

β-[1-methyl-3-[1-methyl-3-[1-methyl-4-[1-methyl-4-[4-N,N-bis2-chloroethyl)amino-benzene-1-carboxamido]imidazole-2-carboxamido]pyrrole-2-carboxamido]pyrazole-5-carboxamido]pyrazole-5-carboxamido]propionamidine, hydrochloride (Compound no. 30);

β-[1-methyl-3-[1-methyl-3-[1-methyl-4-[3-[4-N,N-bis(2-chloroethyl)amino-benzene-1-carboxamido]1,2,4,triazole-5-carboxamido]pyrrole-2-carboxamido]pyrazole-5-carboxamido]pyrazole-5-carboxamido]propionamidine, hydrochloride (Compound no. 31);

β-[1-methyl-3-[1-methyl-3-(l-methyl-4-[1-methyl-4-[4-N,N-bis2-chloroethyl)amino-benzene-1-carboxamido]pyrrole-2-carboxamido]pyrrole-2-carboxamido]pyrazole-5-carboxamido]pyrazole-5-carboxamido]propionamidine, hydrochloride (Compound no. 32).

EXAMPLE 5

β-[1-methyl-3-[1-methyl-4-[1-methyl-4-[4-N,N-bis(2-chloroethyl)amino-benzene-1-carboxamido]pyrrole-2-carboxamido]pyrrole-2-carboxamido]pyrazole-5-carboxamido]propionamidine, hydrochloride (Compound no. 3)

Step one—The intermediate β-[1-methyl-3-[1-methyl-4-nitropyrrole-2-carboxamido]pyrazole-5-carboxamido]propionamidine, hydrochloride.

0.88 g of 1-methyl-4-nitropyrrole-2-carboxyl chloride (prepared as reported in Tetrahedron 34,2389–2391,1978) was added in small portions to a solution of 1.06 g of N-(2'-cyanoethyl)-3-amino-1-methylpyrazole-5-carboxamide (prepared as in Anti Cancer Drug Des. 6,501–517,1991) and 0.72 ml of triethylamine in 20 ml of dioxane. The mixture was stirred overnight, concentrated to small volume, diluted with 30 ml of 5% hydrochloride acid and extracted with ethyl acetate. The organic phase was dried over anhydrous sodium sulphate and after evaporation of the solvent the solid residue was purified by recrystallization from ethyl acetate-hexane, yielding 0.8 g of β-[1-methyl-3-[1-methyl-4-nitropyrrole-2-carboxamido]pyrazole-5-carboxamido]propionitrile. 0.8 g of derivative was suspended in anhydrous ethanol and the solution saturated with dry HCl gas. After 24 h at room temperature, the solvent was evaporated in vacuo and the residue treated with ammonia in ethanol. After 24 h at room temperature the solvent was evaporated in vacuo and the solid residue purified by recryitallization from ethanol absolute yielding 0.79 g of intermediate.

m.p. 180°–183° C.

PMR(DMSO-d$_6$) δ: 9.42 (s,1H), 8.99 (b.s.,2H), 8.92 (b.s.,1H), 8.68 (b.s.,2H), 8.22 (d,J=1.8HZ,1H), 7.80 (d,J=1.8HZ,1H), 7.29 (s,1H), 4.01 (s,3H), 3.95 (s,3H), 3.52 (t,J=6 Hz,2H), 2.62 (t,J=6 Hz,2H).

Step two—The title compound 0.30 g of intermediate was dissolved in a mixture of methanol-dioxane-10% hydrochloride acid (4:1:1) and reduced over Pd catalyst (10% on charcoal) under hydrogen pressure (50 psi) in a Parr apparatus. The solution obtained after filtration of the catalyst was evaporated in vacuo, the solid residue obtained was dissolved in 5 ml of dry dimethylformamide and added of 0.29 g of 1-methyl-4-[4-N,N-bis (2-chloroethyl)amino-benzene-1-carboxamido]pyrrole-2- carboxylic acid (prepared as in Example 1), 0.2 g of 1-ethyl-3-(3'-dimethylaminopropyl)carbodiimide hydrochloride and 0.13 ml of N,N'-diisopropylethylanine. The mixture was stirred overnight at room temperature and brought to pH 4–5 with 10% hydrochloric acid. After evaporation of solvent the solid residue was purified by HPLC using as eluant a mixture of acetonitrile-water-trifluoroacetic acid (10-90-0.1), yielding 0.27 g of the title compound.

FAB-MS: m/z 698,(40,[M+H]$^+$);696,(10,[M–H]$^-$);660, (5,[M–HCl–H]$^-$); 732(10,[M+HCl–H]$^-$)

m.p. 206°–210° C.

U.V. (EtOH 95%): λ max 312.85, ε=39690; λ max 228.70, ε=28388

PMR(DMSO-d$_6$) δ: 10.56 (s,1H), 10.03 (s,1H), 9.97 (s,1H), 8.75 (t,J=5.9 Hz,1H), 9.0 (b.s.,2H), 8.6 (b.s.,2H), 7.84 (m,2H), 7.26 (s,1H), 7.36 (d,J=1.8 Hz,1H), 7.30 (d,J=1.8 Hz,1H), 7.12 (d,J=1.8 Hz,1H), 7.08 (d,J=1.8 Hz,1H), 6.82 (m,2H), 3.99 (s,3H), 3.84 (s,6H), 3.6–3.9 (m,8H), 3.53 (m,2H), 2.61 (m,2H).

By analogous procedure and using the opportune starting material the following compounds can be prepared:

β-[1-methyl-3-[1-methyl-4-[1-methyl-3-[4-N,N-bis(2-chloroethyl)amino-benzene-1-carboxamido]pyrazole-5-carboxamido]pyrrole-2-carboxamido]pyrazole-5-carboxamido]propionamidine, hydrochloride (Compound no. 33);

β-[1-methyl-3-[1-methyl-4-[2-[4-N,N-bis(2-chloroethyl)amino-benzene-1-carboxamido]thiazole-4-carboxamido]pyrrole-2-carboxamido]pyrazole-5-carboxamido]propionamidine, hydrochloride (Compound no. 5)

FAB-MS: m/z 702,(60,[M+H]$^+$); 244,(100); 738,(15)

PMR(DMSO-d$_6$) δ: 12.50 (s,1H), 10.57 (s,1H), 9.75 (s,1H), 9.0 (b.s.,2H), 8.77 (m,1H), 8.7 (b.s.,2H), 8.03 (m,2H), 7.91 (s,1H), 7.28 (s,1H), 7.43 (d,J=1.8 Hz,1H), 7.13 (d,J=1.8 Hz,1H), 6.87 (m,2H), 4.0 (s,3H), 3.87 (s,3H), 3.6–3.9 (m,8H), 3.54 (m,2H), 2.61 (m,2H).

β-[1-methyl-3-[1-methyl-4-[1-methyl-4-[4-N,N-bis(2-chloroethyl)amino-benzene-1-carboxamido]imidazole-2-carboxamido]pyrrole-2-carboxamido]pyrazole-5-carboxamido]propionamidine, hydrochloride (Compound no. 34);

β-[1-methyl-3-[1-methyl-4-[3-[4-N,N-bis(2-chloroethyl)amino-benzene-1-carboxamido]1,2,4,triazole-5-carboxamido]pyrrole-2-carboxamido]pyrazole-5-carboxamido]propionamidine, hydrochloride (Compound no. 35);

β-[1-methyl-3-[1-methyl-4-[1-methyl-4-[4-N,N-bis(2-bromoethyl)amino-benzene-1-carboxamido]pyrrole-2-carboxamido]pyrrole-2-carboxamido]pyrazole-5-carboxamido]propionamidine, hydrobromide (Compound no. 74).

EXAMPLE 6

β-[1-methyl-3-[1-methyl-4-[1-methyl-4-[1-methyl-3-[4-N,N-bis(2-chloroethyl)amino-benzene-1-carboxamido]pyrazole-5-carboxamido]pyrrole-2-carboxamido]pyrrole-2-carboxamido]pyrazole-5-carboxamido]propionamidine,hydrochloride
(Compound no. 36)

Step one—The intermediate β-[1-methyl-3-[1-methyl-4-[1-methyl-4-aminopyrrole-2-carboxamido]pyrrole-2-carboxamido]pyrazole-5-carboxamido]propionamidine, dihydrochloride A solution of 0.57 g of 1-methyl-4-nitropyrrole-2-carboxyl chloride (prepared as reported in Tetrahedron 34,2389,1978) in 10 ml of dioxane was added slowly to a solution of 0.29 g of β-[1-methyl-3-[1-methyl-4-[1-methyl-4-aminopyrrole-2-carboxamido]pyrazole-5-carboxamido]propionamidine,dihydrochloride [prepared as in Example 5] and 0.2 g of sodium bicarbonate in 10 ml of water. The mixture was stirred for two hours, the solvent was evaporated in vacuo and the solid residue chromatographed on silica gel eluting with a mixture of methylene chloride-methanol (80:20 by volume) to yield 0.27 g of β-[1-methyl-3-[1-methyl-4-[1-methyl-4-nitropyrrole-2-carboxamido] pyrrole-2-carboxamido]pyrazole-5-carboxamido] propionamidine, hydrochloride.

The derivative (0.27 g) was dissolved in a mixture of methanol-dioxane-10% hydrdrochloric acid (4:1:1) and reduced over Pd catalyst (10% on charcoal) under hydrogen pressure (50 psi) in a Parr apparatus. The solution obtained after filtration of the catalyst was evaporated in vacuo and the solid residue used in the next step without purification.

Step two—The title compound

A solution of 0.2 g of 1-methyl-3-[4-N,N-bis(2-chloroethyl)amino-benzene-1-carboxamido]pyrazole-5-carboxylic acid (prepared as in Example 1) in 20 ml of dry dimethylformamide was added 0.27 g of intermediate, 0.17 ml of N,N'-diisopropylethylamine and 0.13 g of 1-ethyl-3-(3'-dimethylaminopropyl)carbodiimide hydrochloride. The mixture was stirred at room temperature overnight and brought to pH 4–5 with 10% hydrochloric acid.

After evaporation of solvent a solid residue was obtained which was purified by HPLC using as eluant a mixture of acetonitrile-water-trifluoroacetic acid (10-90-0.1), yielding 0.26 g of the title compound.

FAB-MS: m/z 821,(20,[M+H]$^+$)

PMR(DMSO-d$_6$) δ: 10.91 (s,1H), 10.64 (s,1H), 10.48 (s,1H), 10.01 (s,1H), 9.0 (b.s.,2H), 8.72 (t,J=5.8 Hz,1H), 8.65 (b.s.,2H), 7.93 (m,2H), 7.46 (s,1H), 7.40 (d,J=1.8 Hz,1H), 7.24 (d,J=1.8 Hz,1H), 7.29 (s,1H), 7.18 (d,J=1.8 Hz,1H), 7.11 (d,J=1.8 Hz,1H), 6.81 (m,2H), 4.05 (s,3H), 4.03 (s,3H), 3.86 (s,3H), 3.84 (s,3H), 3.7–3.9 (m,8H), 3.52 (m,2H), 2.62 (m,2H).

By analogous procedure the following compounds can be prepared:

β-[1-methyl-3-[1-methyl-4-[1-methyl-4-[1-methyl-4-[4-N,N-bis(2-chloroethyl)amino-benzene-1-carboxamido]imidazole-2-carboxamido]pyrrole-2-carboxamido]pyrrole-2-carboxamido]pyrazole-5-carboxamido]propionamidine, hydrochloride (Compound no. 37);

β-[1-methyl-3-[1-methyl-4-[1-methyl-4-[3-[4-N,N-bis(2-chloroethyl)amino-benzene-1-carboxamido]1,2,4,triazole-5-carboxamido]pyrrole-2-carboxamido]pyrrole-2-carboxamido]pyrazole-5-carboxamido]propionamidine, hydrochloride (Compound no. 38);

β-[1-methyl-3-[1-methyl-4-[1-methyl-4-[1-methyl-4-[4-N,N-bis(2-chloroethyl)amino-benzene-1-carboxamido]pyrrole-2-carboxamido]pyrrole-2-carboxamido]pyrrole-2-carboxamido]pyrazole-5-carboxamido]propionamidine, hydrochloride (Compound no. 39).

EXAMPLE 7

β-[1-methyl-3-[1-methyl-4-[1-methyl-3-[1-methyl-3-[4-N,N-bis(2-chloroethyl)amino-benzene-1-carboxamido]pyrazole-5-carboxamido]pyrazole-5-carboxamido]pyrrole-2-carboxamido]pyrazole-5-carboxamido]propionamidine, hydrochloride
(Compound no. 40)

Step one—The intermediate β[1-methyl-3-[1-methyl-4-[1-methyl-3-aminopyrazole-5-carboxamido]pyrrole-2-carboxamido]pyrazole-5-carboxamido]propionamidine, dihydrochloride To a solution of 0.2 g of 3-(benzyloxycarbonyl)amino-1-methylpyrazole-5-carboxylic acid (prepared as reported in J.

Org. Chem. 54,431–434,1989) in 20 ml of dry dimethylformamide was added 0.2 g of β-[1-methyl-3-[1-methyl-4-aminopyrrole-2-carboxamido]pyrazole-5-carboxamido] propionamidine, dihydrochloride [prepared as in Example 5], 0.2 ml triethylamine and 0.14 g of 1-ethyl-3-(3'-dimethylaminopropyl)carbodiimide hydrochloride.

The mixture was stirred overnight, the solvent was evaporated in vacuo and the solid residue chromatographed on silica gel eluting with a mixture methylene chloride-methanol (80:20 by volume), yielding 0.28 g of β-[1-methyl-3-[1-methyl-4-[1-methyl-3-(benzyloxicarbonyl) aminopyrazole-5-carboxamido]pyrrole-2-carboxamido] pyrazole-5-carboxamido]propionamidine, hydrochloride.

The derivative (0.28 g) was dissolved in a mixture of methanol-dioxane-10% hydrdrochloric acid (4:1:1) and reduced over Pd catalyst (10% on charcoal) under hydrogen pressure (50 psi) in a Parr apparatus. The solution obtained after filtration of the catalyst was evaporated in vacuo and the solid residue used in the next step without purification.
Step two—The title compound A solution of 0.2 g of 1-methyl-3-[4-N,N-bis(2-chloroethyl)amino-benzene-1-carboxamido]pyrazole-5-carboxylic acid (prepared as in Example 1) in 20 ml of dry dimethylformamide was added 0.27 g of intermediate, 0.17 ml of N,N'-diisopropylethylamine and 0.18 g of 1-ethyl-3-(3'-dimethylaminopropyl)carbodiimide hydrochloride. The mixture was stirred at room temperature overnight and brought to pH 4–5 with 10% hydrochloric acid.

After evaporation of solvent a solid residue was obtained which was purified by HPLC using as eluant a mixture of acetonitrile-water-trifluoroacetic acid (10-90-0.1), yielding 0.26 g of the title compound.

FAB-MS: m/z 822,(23,[M+H]$^+$)

PMR(DMSO-d$_6$) δ: 11.1 (s,1H), 10.5 (s,1H), 10.3 (s,1H), 10.02 (s,1H), 8.96 (b.s.,2H), 8.8 (t,J=5.8 Hz,1H), 8.65 (b.s.,2H), 7.94 (m,2H), 7.53 (s,1H), 7.42 (s,1H), 7.37 (s,1H), 7.31 (d,J=1.8 Hz,1H), 7.24 (d,J=1.8 Hz,1H), 6.82 (m,2H), 4.04 (s,3H), 4.02 (s,3H), 3.86 (s,3H), 3.84 (s,3H), 3.6–3.9 (m,8H), 3.52 (m,2H), 2.6 (m,2H).

By analogous procedure the following compounds can be prepared:

β-[1-methyl-3-[1-methyl-4-[1-methyl-3-[1-methyl-4-[4-N,N-bis(2-chloroethyl)amino-benzene-1-carboxamido] pyrrole-2-carboxamido]pyrazole-5-carboxamido]pyrrole-2-carboxamido]pyrazole-5-carboxamido] propionamidine,hydrochloride (Compound no. 41);

β-[1-methyl-3-[1-methyl-4-[1-methyl-3-[1-methyl-4-[4-N,N-bis(2-chloroethyl)amino-benzene-1-carboxamido] imidazole-2-carboxamido]pyrazole-5-carboxamido] pyrrole-2-carboxamido]pyrazole-5-carboxamido] propionamidine, hydrochloride (Compound no. 42);

β-[1-methyl-3-[1-methyl-4-[1-methyl-3-[3-[4-N,N-bis(2-chloroethyl)amino-benzene-1-carboxamido]1,2,4, triazole-5-carboxamido]pyrazole-5-carboxamido] pyrrole-2-carboxamido]pyrazole-5-carboxamido] propionamidine, hydrochloride (Compound no. 43).

EXAMPLE 8

β-[1-methyl-3-[1-methyl-3-[1-methyl-3-[4-N,N-bis (2-chloroethyl)amino-benzene-1-carboxamido] pyrazole-5-carboxamido]pyrazole-5-carboxamido] pyrazole-5-carboxamido]propionamidine, hydrochloride (Compound no. 7)

Step one—The intermediate 1-methyl-3-nitropyrazole-5-carboxylic acid

A solution of 0.8 g of methyl 1-methyl-3-aminopyrazole-5-carboxylate (prepared as reported in J.Org.Chem. 54,431–434, 1989) in 15 ml of chloroform was added in small portions to a solution of 1.24 g of 3-chloroperbenzoic acid in 30 ml of chloroform and refluxed for two hours. The mixture was cooled, the solid residue filtered, the solution washed for three time with 10% sodium hydroxide and dried over anhydrous sodium sulphate.

After evaporation of solvent in vacuo the solid residue was purified by recrystallization from ethyl acetate-petroleum ether to yield 0.5 g of methyl 1-methyl-3-nitropyrazole-5-carboxylate. The derivative (0.5 g) was dissolved in 7 ml of dioxane and added of 3 ml of 2N potassium hydroxide. The mixture was stirred for two hours, acidified with 10% hydrochloridric acid and the solvent evaporated in vacuo. The solid residue was dissolved in ethyl acetate, washed with water and dried over anhydrous sodium sulphate. After evaporation of solvent 0.4 g of intermediate was obtained.

m.p. 165°–167° C.

PMR(DMSO-d6) δ: 7.57 (b.s.,1H), 7.37 (s,1H), 4.27 (s,3H).

Step two—The intermediate β-(1-methyl-3-(1-methyl-3-(1-methyl-3-nitropyrazole-5-carboxamido)pyrazole-5-carboxamido)pyrazole-5-carboxamido)propionitrile To a solution of 0.2 g of intermediate and 0.412 g of β-[1-methyl-3-[1-methyl-3-aminopyrazole-5-carboxamido] pyrazole-5-carboxamido]propionitrile (prepared as reported in Anti Cancer Drug Des.6,501–517,1991) in 30 ml of dry dimethylformamide was added 0.43 g of 1-ethyl-3-(3'-dimethylaminopropyl)carbodiimide hydrochloride and 0.86 ml of N,N'-diisopropylethylamine. The mixture was stirred at room temperature overnight and the solvent was evaporated in vacuo. The solid residue obtained was dissolved in ethyl acetate and washed with solution of 10% hydrochloridric acid. The organic phase was dried over anhydrous sodium sulphate, the solvent was evaporated in vacuo to yield a solid which was purified by recrystallization from ethyl acetate-petroleum ether, yielding 0.323 g of intermediate.

Step three—The intermediate β-(1-methyl-3-(1-methyl-3-(1-methyl-3-aminopyrazole-5-carboxamido)pyrazole-5-carboxamido)pyrazole-5-carboxamido)propionamidine, dihydrochloride 0.3 g of intermediate was suspended in anhydrous ethanol and the solution saturated with dry HCl gas. After 24 h at room temperature, the solvent was evaporated in vacuo and the residue treated with ammonia in ethanol. After 24 h at room temperature the solvent was evaporated in vacuo and the solid residue purified by recrystallization from ethanol absolute to yield 0.2 g of amidine derivative which was dissolved in a mixture of methanol-dioxane-10% hydrdrochloric acid (4:1:1) and reduced over Pd catalyst (10% on charcoal) under hydrogen pressure (50 psi) in a Parr apparatus.

The solution obtained after filtration of the catalyst was evaporated in vacuo and the solid residue purified by recrystallization from ethyl acetate-ether, yielding 0.17 g of intermediate.

PMR(DMSO-d6) δ: 11.31 (s,1H), 11:17 (s,1H), 9.15–8.85 (bs,7H), 8.63 (b.s.,1H), 7.59 (s,1H), 7.31 (s,1H), 7.13 (s,1H), 4.09 (s,3H), 4.07 (s,3H), 4.01 (s,3H), 3.54 (t,J=6 Hz,2H), 2.73 (t,J=6 Hz,2H),

Step four—The title compound

To a solution of 0.3 g of intermediate in 20 ml of water and 0.14 g of sodium bicarbonate was added slowly a solution of 0.3 g of 4-N,N-bis(2-chloroethyl)aminobenzoyl chloride (prepared as in J. Org. Chem.26,4996–4997,1961) in 20 ml of dioxane.

The mixture was stirred for one hour at room temperature and brought to pH 4–5 with 10% hydrochloric acid.

After evaporation of the solvent a solid residue was obtained which was purified by HPLC using as eluant a mixture of acetonitrile-water-trifluoroacetic acid (10-90-0.1), yielding 0.18 g of the title compound.

FAB-MS: m/z 700,(20,[M+H]$^+$)

U.V. (EtOH 95%): λ max 306.9, ε=23142

PMR(DMSO-d$_6$) δ: 11.12 (b.s.,2H), 10.68 (s,1H), 8.92 (t,J=5.8 Hz,1H), 8.64 (b.s.,4H), 7.95 (m,2H), 7.61 (s,1H), 7.52 (s,1H), 7.32 (s,1H), 6.81 (m,2H), 4.03 (s,3H), 4.02 (s,3H), 4.00 (s,3H), 3.6–4.0 (m,8H), 3.53 (m,2H), 2.71 (m,2H).

By analogous procedure the following compound can be prepared:

β-[1-methyl-3-[1-methyl-3-[1-methyl-3-[1-methyl-3-[4-N,N-bis(2-chloroethyl)amino-benzene-1-carboxamido]pyrazole-5-carboxamido]pyrazole-5-carboxamido]pyrazole-5-carboxamido]pyrazole-5carboxamido]propionamidine, hydrochloride (Compound no. 15).

EXAMPLE 9

β-[1-methyl-4-[1-methyl-4-[1-methyl-3-[1-methyl-3-[4-N,N-bis(2-chloroethyl)amino-benzene-1-carboxamido]pyrazole-5-carboxamido]pyrazole-5-carboxamido]pyrrole-2-carboxamido]pyrrole-2-carboxamido]propionamidine, hydrochloride (Compound no. 29)

Step one—The intermediate β-[1-methyl-4-[1-methyl-4-[1-methyl-3-aminopyrazole-5-carboxamido]pyrrole-2-carboxamido]pyrrole-2-carboxamido]propionamidine, dihydrochloride To a solution of 0.55 g of 1-methyl-3-nitropyrazole-5-carboxylic acid (prepared as in reported in Example 8) in 10 ml of benzene were added 2 ml of thionyl chloride. The mixture was refluxed for one hour and the solvent evaporated in vacuo to yield a solid residue which was dissolved in 10 ml of dioxane and added in small portions to a solution of 1 g of β-[1-methyl-4-[1-methyl-4-aminopyrrole-2-carboxamido]pyrrole-2-carboxamido]propionamidine, dihydrochloride (prepared as reported in J. Med. Chem. 32,774–778,1989) and 0.2 g of sodium bicarbonate in 10 ml of water. The mixture was stirred for one hour and then brought to pH 4–5 with 10% hydrochloric acid. The Solvent was evaporated in vacuo and the solid residue chromatographed on silica gel eluting whit a mixture methylene chloride-methanol (80:20 by volume), yielding 0.7 g of β-[1-methyl-4-[1-methyl-4-[1-methyl-3-nitropyrazole-5-carboxamido]pyrrole-2-carboxamido]pyrrole-2-carboxamido]propionamidine, hydrochloride.

The nitro derivative (0.7 g) was dissolved in a mixture of methanol-dioxane-10% hydrdrochloric acid (4:1:1) and reduced over Pd catalyst (10% on charcoal) under hydrogen pressure (50 psi) in a parr apparatus.

The solution obtained after filtration of the catalyst was evaporated in vacuo and the solid residue (0.6 g) used in the next step without purification.

Step two—The title compound

A solution of 0.7 g of 1-methyl-3-[4-N,N-bis(2-chloroethyl)amino-benzene-1-carboxamido]pyrazole-5-carboxylic acid (prepared as reported in Example 1) in 20 ml of dry dimethylformamide was added 0.6 g of intermediate, 0.24 ml of N-N'-diisopropylethylamine and 0.5 g of 1-ethyl-3-(3'-dimethylaminopropyl)carbodiimide hydrochloride.

The reaction mixture was stirred overnight at room temperature and brought to pH 4–5 with 10% hydrochloric acid. The Solvent was evaporated in vacuo to yield a solid residue which was purified by HPLC using as eluant a mixture of acetonitrile-water-trifluoroacetic acid (10:90:0.1) to yield 0.7 g of the title compound.

By analogous procedure the following compounds can be prepared:

β-[1-methyl-4-[1-methyl-4-[1-methyl-3-[1-methyl-4-[4-N,N-bis(2-chloroethyl)amino-benzene-1-carboxamido]imidazole-2-carboxamido]pyrazole-5-carboxamido]pyrrole-2-carboxamido]pyrrole-2-carboxamido]propionamidine, hydrochloride (Compound no. 65);

β-[1-methyl-4-[1-methyl-4-[1-methyl-3-[1-methyl-4-[4-N,N-bis(2-chloroethyl)amino-benzene-1-carboxamido]pyrrole-2-carboxamido]pyrazole-5-carboxamido]pyrrole-2-carboxamido]pyrrole-2-carboxamido]propionamidine, hydrochloride (Compound no. 66).

EXAMPLE 10

β-[1-methyl-4-[1-methyl-3-[1-methyl-3-[4-N,N-bis(2-chloroethyl)amino-benzene-1-carboxamido]pyrazole-5-carboxamido]pyrazole-5-carboxamido]pyrrole-2-carboxamido]propionamidine, hydrochloride (Compound no. 67)

Step one—The intermediate β-[1-methyl-4-[1-methyl-3-nitropyrazole-5-carboxamido]pyrrole-2-carboxamido]propionamidine, hydrochloride.

A solution of 0.89 g of 1-methyl-3-nitropyrazole-2-carboxyl chloride (prepared as reported in Example 8) in 10 ml of dioxane was added in small portions to a solution of 1 g of 3-(1-methyl-4-aminopyrrole-2-carboxamido)propionitrile (prepared as reported in J. Org. Chem. 55,728–737,1990) and 0.95 ml of triethylamine in 10 ml of dioxane.

The mixture was stirred overnight, concentrated to small volume, diluted with 30 ml of 5% hydrochloride acid and extracted with ethyl acetate. The organic phase was dried over anhydrous sodium sulphate and after evaporation of the solvent the solid residue was purified by recrystallization from ethyl acetate-hexane, yielding 0.9 g of β-[1-methyl-4-[1-methyl-3-nitropyrazole-5-carboxamido]pyrrole-2-carboxamido]propionitrile. 0.9 g of derivative was suspended in anhydrous ethanol and the solution saturated with dry HCl gas. After 24 h at room temperature, the solvent was evaporated in vacuo and the residue treated with ammonia in ethanol. After 24 h at room temperature the solvent was evaporated in vacuo and the solid residue purified by recrystallization from ethanol absolute yielding 0.8 g of intermediate.

Step two—The title compound 0.50 g of intermediate was dissolved in a mixture of methanol-dioxane-10% hydrochloride acid (4:1:1) and reduced over Pd catalyst (10% on charcoal) under hydrogen pressure (50 psi) in a parr apparatus. The solution obtained after filtration of the catalyst was evaporated in vacuo, the solid residue obtained was dissolved in 5 ml of dry dimethylformamide and added of 0.48 g of 1-methyl-3-[4-N,N-bis(2-chloroethyl)amino-benzene-1-carboxamido]pyrazole-5-carboxylic acid (prepared as in Example 8), 0.48 g of 1-ethyl-3-(3'-dimethylaminopropyl)carbodiimide hydrochloride and 0.21 ml of N,N'-diisopropylethylamine. The mixture was stirred overnight at room temperature and brought to pH 4–5 with 10% hydrochloric acid. After evaporation of solvent the solid residue was purified by HPLC using as eluant a mixture of acetonitrile-water-trifluoroacetic acid (10-90-0.1), yielding 0.4 g of the title compound.

By analogous procedure the following compounds can be prepared:

β-[1-methyl-4-[1-methyl-3-[1-methyl-4-[4-N,N-bis(2-chloroethyl)amino-benzene-1-carboxamido]pyrrole-2-carboxamido]pyrazole-5-carboxamido]pyrrole-2-carboxamido]propionamidine,hydrochloride (Compound no. 68);

β-[1-methyl-4-[1-methyl-3-[3-[4-N,N-bis(2-chloroethyl)amino-benzene-1-carboxamido]1,2,4,triazole-5-carboxamido]pyrazole-5-carboxamido]pyrrole-2-carboxamido]propionamidine,hydrochloride (Compound no. 10);

β-[1-methyl-4-[1-methyl-3-[1-methyl-4-[4-N,N-bis(2-chloroethyl)amino-benzene-1-carboxamido]imidazole-2-carboxamido]pyrazole-5-carboxamido]pyrrole-2-carboxamido]propionamidine,hydrochloride (Compound no. 9).

EXAMPLE 11

β-(1-methyl-4-(1-methyl-4-(2-(α-bromoacrylamido) thiazole-4-carboxamido)pyrrole-2-carboxamido) pyrrole-2-carboxamido)propionamidine, hydrochloride (Compound no. 16)

Step one—The intermediate 2-(α-bromoacrylamido) thiazole-4-carboxilic acid

To a solution containing 0.688 g of ethyl 2-aminothiazole-4carboxilate (prepared as reported in J.A.C.S. 68,266,1946) and 0.3 g of 2-bromoacrylic acid in 10 ml of dioxane, 0.412 g of N-N'dicyclohexylcarbodiimide were and the mixture was stirred at room temperature overnight. After filtration, the solvent was evaporated in vacuo, the solid residue was dissolved in 50 ml of ethyl acetate, treated with saturated solution of sodium bicarbonate and then with 10% hydrochloric acid. The organic phase was dried over anhydrous sodium sulphate and the solvent evaporated in vacuo. The solid residue was purified by recrystallization from ethanol-water to yield 0.52 g of ethyl 2-(α-bromoacrylamido) thiazole-4-carboxylate.

The derivative (0.52 g) was dissolved in 10 ml of dioxane and added of 1.6 ml of 2N potassium hydroxide, the mixture was stirred overnight, acidified with 10% hydrochloric acid and the solvent was evaporated in vacuo yielding 0.45 g of intermediate.

m.p. 227°–229° C.

PMR(DMSO-d$_6$) δ 3.04 (b.s.,1H), 8.15 (s,1H), 8.06 (s,1H), 7.06 (d,J=3.7 Hz,1H), 6.54 (d,J=3.7 Hz,1H).

By analogous procedure the following compounds can be prepared:

1-methyl-4-(α-bromoacrylamido)pyrrole-2-carboxylic acid

PMR(DMSO-d$_6$) δ: 12.2 (b.s.,1H), 10.2 (s, 1H), 7.38 (d,J=1.8 Hz,1H) , 6.85 (d,J=1.8 Hz,1H), 6.68 (d,J=3.7 Hz,1H), 6.2 (d,J=3.7 Hz,1H), 3.82 (s,3H).

1-methyl-3-(α-bromoacrylamido)pyrazole-5-carboxylic acid

PMR(DMSO-d$_6$) δ: 12.9 (b.s.,1H), 10.1 (s, 1H), 7.22 (s,1H), 6.95 (d,J=3.7 Hz,1H), 6.43 (d,J=3.7 Hz,1H), 4.02 (s,3H).

1-methyl-4-(α-bromoacrylamido)imidazole-2-carboxylic acid 3-(α-bromoacrylamido)1,2,4,triazole-5-carboxylic acid Step two—The title compound To a solution containing 0.21 g of β-[1-methyl-4-[1-methyl-4-aminopyrrole-2-carboxamido]pyrrole-2-carboxamido]propionamidine, dihydrochloride (prepared as reported in J. Med. Chem. 32,774–778,1989) in 10 ml of dry dimethylformamide, 0.15 g of intermediate, 0.153 g of 1-ethyl-3-(3'dimethylaminopropyl)carbodiimide hydrochloride and 0.09 ml of N,N'-diisopropylethylamine were added.

The mixture was stirred overnight at room temperature and brought to pH 4–5 with 10% hydrochloric acid.

After evaporation of the solvent a solid residue was obtained which was purified by HPLC using as eluant a mixture of acetonitrile-water-trifluoroacetic acid (10-90-0.1), yielding 0.13 g of the title compound.

FAB-MS: m/z 592,(40,[M+H]$^+$)

PMR(DMSO-d$_6$) δ: 10.00 (s,1H), 9.88 (s,1H), 8.98 (b.s., 2H), 8.63 (b.s.,2H), 8.23 (t,J=5.8 Hz,1H), 7.99 (s,1H), 7.28 (d,J=1.8 Hz,1H), 7.20 (d,J=1.8 Hz,1H), 7.10 (d,J=1.8 Hz,1H), 7.04 (d,J=3.7 Hz,1H), 6.95 (d,J=1.8 Hz,1H), 6.54 (d,J=3.7 Hz,1H), 3.85 (s,3H), 3.8 (s,3H), 3.48 (m,2H), 2.61 (m,2H).

By analogous procedure and using opportune intermediate prepared as described above, the following compounds can be prepared:

β-(1-methyl-4-(1-methyl-4-(1-methyl-3-(α-bromoacrylamido)pyrazole-5-carboxamido)pyrrole-2-carboxamido)pyrrole-2-carboxamido)propionamidine, hydrochloride (Compound no. 17)

FAB-MS: m/z 587,(8,[M+H]$^+$)

PMR(DMSO-d$_6$) δ: 11.03 (s,1H), 10.48 (s,1H), 9.98 (s,1H), 9.00 (b.s.,2H), 8.6 (b.s.,2H), 8.22 (t,J=5.8 Hz,1H), 7.35 (s,1H), 7.3 (d,J=1.8 Hz,1H), 7.19 (d,J=1.8 Hz,1H), 7.08 (d,J=1.8 Hz,1H), 6.94 (d,J=1.8 Hz,1H), 6.80 (d,J=3.7 Hz,1H), 6.32 (d,J=3.7 Hz,1H), 4.04 (s,3H), 3.85 (s,3H), 3.8 (s,3H), 3.5 (m,2H), 2.6 (m,2H).

β-(1-methyl-4-(1-methyl-4-(3-(α-bromoacrylamido)1,2,4, triazole-5-carboxamido)pyrrole-2-carboxamido)pyrrole-2-carboxamido)propionamidine, hydrochloride (Compound no. 18);

β-(1-methyl-4-(1-methyl-4-(1-methyl-4-(α-bromoacrylamido)imidazole-2-carboxamido)pyrrole-2-carboxamido)pyrrole-2-carboxamido)propionamidine, hydrochloride (Compound no. 22);

β-(1-methyl-4-(1-methyl-4-(1-methyl-4-(1-methyl-3(α-bromoacrylamido)pyrazole-5-carboxamido)pyrrole-2-carboxamido)pyrrole-2-carboxamido)pyrrole-2-carboxamido)propionamidine, hydrochloride (Compound no. 28)

FAB-MS: m/z 709,(7,[M+H]$^+$)

PMR(DMSO-d$_6$) δ: 11.02 (s,1H), 10.48 (s,1H), 10.00 (s,1H), 9.92 (s,1H), 8.9 (b.s.,2H), 8.5 (b.s.,2H), 8.21 (m,1H), 7.35 (s,1H), 7.30 (d,J=1.8 Hz,1H), 7.24 (d,J=1.8 Hz,1H), 7.17 (d,J=1.8 Hz,1H), 7.09 (d,J=1.8 Hz,1H), 7.06 (d,J=1.8 Hz,1H), 6.95 (d,J=1.8 Hz,1H), 6.79 (d,J=3.4 Hz,1H), 6.31 (d,J=3.4 Hz,1H), 4.04 (s,3H), 3.86 (s,3H), 3.83 (s,3H), 3.8 (s,3H), 3.49 (m,2H), 2.59 (m,2H).

β-(1-methyl-4-(1-methyl-4-(1-methyl-4(2-(α-bromoacrylamido)thiazole-4-carboxamido)pyrrole-2-carboxamido)pyrrole-2-carboxamido)pyrrole-2-carboxamido)propionamidine,hydrochloride (Compound no. 44);

β-(1-methyl-4-(1-methyl-4-(1-methyl-4-(3-(α-bromoacrylamido)1,2,4,triazole-5-carboxamido)pyrrole-2-carboxamido)pyrrole-2-carboxamido)pyrrole-2-carboxamido)propionamidine,hydrochloride (Compound no. 45);

β-(1-methyl-4-(1-methyl-4-(1-methyl-4-(1-methyl-4-(α-bromoacrylamido)imidazole-2-carboxamido)pyrrole-2-carboxamido)pyrrole-2-carboxamido)pyrrole-2-carboxamido)propionamidine, hydrochloride (Compound no. 46)

FAB-MS: m/z 709, (15, [M+H]⁺) ; 256
U.V. (EtOH 95%): λ max 312.85, ε=41902; λ max 239.9, ε=24543
PMR(DMSO-d₆) δ: 10.09 (s,1H), 10.06 (b.s.,1H), 9.99 (s,1H), 9.91 (s,1H), 8.9 (b.s.,4H), 8.23 (t,J=5.9 Hz,1H), 7.52 (s,1H), 7.26 (d,J=1.8 Hz,1H), 7.23 (d,J=1.8 Hz,1H), 7.17 (d,J=1.8 Hz,1H), 7.16 (d,J=1.8 Hz,1H), 7.06 (d,J=1.8 Hz,1H), 6.93 (d,J=1.8 Hz,1H), 6.80 (d,J=3.1 Hz,1H), 6.29 (d,J=3.1 Hz,1H), 3.97 (s,3H), 3.84 (s, H), 3.83 (s,3H), 3.79 (s,3H), 3.49 (m,2H), 2.61 (t,J=6.2 Hz,2H).

β-(1-methyl-3-(1-methyl-3-(1-methyl-4-(α-bromoacrylamido)pyrrole-2-carboxamido]pyrazole-5-carboxamido]pyrazole-5-carboxamido]propionamidine, hydrochloride (Compound no. 19);

β-(1-methyl-3-(1-methyl-3-(1-methyl-4-(α-bromoacrylamido)imidazole-2-carboxamido)pyrazole-5-carboxamido)pyrazole-5-carboxamido)propionamidine, hydrochloride (Compound no. 47);

β-(1-methyl-3-(1-methyl-3-(2-(α-bromoacrylamido)thiazole-4-carboxamido)pyrazole-5-carboxamido)pyrazole-5-carboxamido)propionamidine, hydrochloride (Compound no. 48);

β-(1-methyl-3-(1-methyl-3-(3-(α-bromoacrylamido)1,2,4,triazole-5-carboxamido)pyrazole-5-carboxamido)pyrazole-5-carboxamido)propionamidine, hydrochloride (Compound no. 49);

β-(1-methyl-3-(1-methyl-3-(1-methyl-3-(α-bromoacrylamido)pyrazole-5-carboxamido)pyrazole-5-carboxamido)pyrazole-5-carboxamido)propionamidine, hydrochloride (Compound no. 23);

β-(1-methyl-3-(1-methyl-3-(1-methyl-4-(1-methyl-3-(α-bromoacrylamido)pyrazole-5-carboxamido)pyrrole-2-carboxamido)pyrazole-5-carboxamido)pyrazole-5-carboxamido)propionamidine, hydrochloride (Compound no. 50);

β-(1-methyl-3-(1-methyl-3-(1-methyl-4-(1-methyl-4-(α-bromoacrylamido)imidazole-2-carboxamido)pyrrole-2-carboxamido)pyrazole-5-carboxamido)pyrazole-5-carboxamido)propionamidine, hydrochloride (Compound no. 51);

β-(1-methyl-3-(1-methyl-3-(1-methyl-4-(1-methyl-4-(α-bromoacrylamido)pyrrole-2-carboxamido)pyrrole-2-carboxamido)pyrazole-5-carboxamido)pyrazole-5-carboxamido)propionamidine, hydrochloride (Compound no. 52);

β-(1-methyl-3-(1-methyl-4-(1-methyl-4-(α-bromoacrylamido)pyrrole-2-carboxamido)pyrrole-2-carboxamido)pyrazole-5-carboxamido)propionamidine, hydrochloride (Compound no. 20);

β-(1-methyl-4-(1-methyl-3-(1-methyl-4-(α-bromoacrylamido)pyrrole-2-carboxamido)pyrazole-5-carboxamido)pyrrole-2-carboxamido)propionamidine, hydrochloride (Compound no. 69);

β-(1-methyl-4-(1-methyl-3-(1-methyl-4-(α-bromoacrylamido)imidazole-2-carboxamido)pyrazole-5-carboxamido)pyrrole-2-carboxamido)propionamidine, hydrochloride (Compound no. 24);

β-(1-methyl-4-(1-methyl-3-(1-methyl-3-(α-bromoacrylamido)pyrazole-5-carboxamido)pyrazole-5-carboxamido)pyrrole-2-carboxamido)propionamidine, hydrochloride (Compound no. 70);

β-(1-methyl-3-(1-methyl-4-(3-(α-bromoacrylamido)1,2,4,triazole-5-carboxamido)pyrazole-5-carboxamido)pyrrole-2-carboxamido)propionamidine,hydrochloride (Compound no. 25);

β-(1-methyl-3-(1-methyl-4-(1-methyl-3-(α-bromoacrylamido)pyrazole-5-carboxamido)pyrrole-2-carboxamido)pyrazole-5-carboxamido)propionamidine, hydrochloride (Compound no. 53);

β-(1-methyl-3-(1-methyl-4-(2-(α-bromoacrylamido)thiazole-4-carboxamido)pyrrole-2-carboxamido)pyrazole-5-carboxamido)propionamidine,hydrochloride (Compound no. 21);

β-(1-methyl-3-(1-methyl-4-(1-methyl-4-(α-bromoacrylamido)imidazole-2-carboxamido)pyrrole-2-carboxamido)pyrazole-5-carboxamido)propionamidine, hydrochloride (Compound no. 54);

β-(1-methyl-3-(1-methyl-4-(1-methyl-4-(1-methyl-3-(αbromoacrylamido)pyrazole-5-carboxamido)pyrrole-2-carboxamido)pyrrole-2-carboxamido)pyrazole-5-carboxamido)propionamidine, hydrochloride (Compound no. 55);

β-(1-methyl-3-(1-methyl-4-(1-methyl-4-(1-methyl-4-(α-bromoacrylamido)imidazole-2-carboxamido)pyrrole-2-carboxamido)pyrrole-2-carboxamido)pyrazole-5-carboxamido)propionamidine,hydrochloride (Compound no. 56);

β-(1-methyl-3-(1-methyl-4-(1-methyl-4-(3-(α-bromoacrylamido)1,2,4,triazole-5-carboxamido)pyrrole-2-carboxamido)pyrrole-2-carboxamido)pyrazole-5-carboxamido)propionamidine,hydrochloride (Compound no. 57);

β-(1-methyl-3-(1-methyl-4-(1-methyl-4-(1-methyl-4-(α-bromoacrylamido)pyrrole-2-carboxamido)pyrrole-2-carboxamido)pyrrole-2-carboxamido)pyrazole-5-carboxamido)propionamidine, hydrochloride (Compound no. 58);

β-(1-methyl-3-(1-methyl-4-(1-methyl-3-(1-methyl-3-(α-bromoacrylamido)pyrazole-5-carboxamido)pyrazole-5-carboxamido)pyrrole-2-carboxamido)pyrazole-5-carboxamido)propionamidine, hydrochloride (Compound no. 59);

β-(1-methyl-3-(1-methyl-4-(1-methyl-3-(1-methyl-4-(α-bromoacrylamido)pyrrole-2-carboxamido)pyrazole-5-carboxamido)pyrrole-2-carboxamido)pyrazole-5-carboxamido)propionamidine, hydrochloride (Compound no. 60);

β-(1-methyl-4-(1-methyl-4-(1-methyl-3-(1-methyl-3-(α-bromoacrylamido)pyrazole-5-carboxamido)pyrazole-5-carboxamido)pyrrole-2-carboxamido)pyrrole-2-carboxamido)propionamidine, hydrochloride (Compound no. 26);

β-(1-methyl-4-(1-methyl-4-(1-methyl-3-(1-methyl-4-(α-bromoacrylamido)pyrrole-2-carboxamido)pyrazole-5-carboxamido)pyrrole-2-carboxamido)pyrrole-2-carboxamido)propionamidine, hydrochloride (Compound no. 71);

β-(1-methyl-4-(1-methyl-4-(1-methyl-3-(1-methyl-4-(α-bromoacrylamido)imidazole-2-carboxamido)pyrazole-5-carboxamido)pyrrole-2-carboxamido)pyrrole-2-carboxamido)propionamidine, hydrochloride (Compound no. 72);

β-(1-methyl-3-(1-methyl-3-(1-methyl-3-(1-methyl-3-(αbromoacrylamido)pyrazole-5-carboxamido)pyrazole-5-carboxamido)pyrazole-5-carboxamido)pyrazole-5-carboxamido)propionamidine, hydrochloride (Compound no. 27).

EXAMPLE 12

β-[1-methyl-3-[1-methyl-3-[1-methyl-4-[4-N,N-bis(2-bromoethyl)amino-benzene-1-carboxamido]pyrrole-2-carboxamido]pyrazole-5-carboxamido]pyrazole-5-carboxamido]propionamidine, hydrobromide (Compound no. 75)

Step one—The intermediate 4-N,N-bis-(2-bromoethyl)amino-1-(1-imidazolylcarbonyl)benzene To a solution of 1.5 g of ethyl 4-N,N-bis-(2-bromoethyl) amino-benzoic acid (prepared as reported in J. Med. Chem. 21,16,1978) in 50 ml of ethyl acetate, were added 850 mg of N-N'carbonyldiimidazol. The solution was stirred at room temperature for 4 hours. The solvent was partially removed in vacuo to afford the intermediate as a white precipitate.

m.p. (EtOAc) 104°–106° C.

PMR(CDCl$_3$) δ: 8.07 (s,1H), 7.76 (m,2H), 7.5 (m,1H), 7.13 (m,1H), 6.73 (m,2H), 3.88 (t,J=7.4 Hz,4H), 3.49 (t,J=7.4 Hz,4H).

By analogous procedure and using the opportune starting material the following compounds can be prepared:

1-methyl-4-[4-N,N-bis(2-bromoethyl)amino-benzene-1-carboxamido]-2-(1-imidazolylcarbonyl) pyrrole PMR(CDCl$_3$) δ: 8.78 (s,1H), 8.22 (s,1H), 7.86 (m,1H), 7.83 (m,2H), 7.58 (m,1H), 7.11 (d,J=1.8 Hz,1H), 6.75 (d,J=1.8 Hz,1H), 6.66 (m,2H), 3.96 (s,1H), 3.82 (t,J=7.3 Hz,4H), 3.45 (t,J=7.3 Hz,4H).

1-methyl-3-[4-N,N-bis(2-bromoethyl)amino-benzene-1-carboxamido]-5-(1-imidazolylcarbonyl) pyrazole Step two—The title compound The intermediate β-[1-methyl-3-[1-methyl-3[1-methyl-4-amino-pyrrole-2-carboxamido]pyrazole-5-carboxamido] pyrazole-5-carboxamido]propionamidine, dihydrochloride (prepared as reported in Step two of Example 3) was transformed into the corresponding diihydrobromide using a strong basic anion exchange resin. The intermediate diihydrobromide (1.02 gr, 1.66 mmole) was dissolved in 20 ml of dry dimethylformamide and 1 gr (2.5 mmole) of 4-N,N-bis (2-bromoethyl)amino-1-(1-imidazolylcarbonyl)benzene was added. The solution was stirred for 4 hours at 50° C., the solvent removed in vacuo and the residue purified by flash chromatography (methylenechloride-methanol 8:2) to yield 950 mg of the title compound.

m.p. 210°–211° C.

FAB-MS: m/z 787,(20,[M+H]$^+$); 332 (30)

PMR(DMSO-d$_6$) δ: 11.17 (s,1H), 10.56 (s,1H), 10.06 (s,1H), 8.95 (s,2H), 8.79 (bs,1H), 8.49 (s,2H), 7.86 (m,2H), 7.54 (s,1H), 7.41 (d,J=1.9 Hz,1H), 7.31 (s,1H), 7.15 (s,J=1.9 Hz,1H), 6.81 (m,2H), 4.05 (s,3H), 4.01 (s,3H), 4.02 (s,3H), 3.88 (m,4H), 3.63 (m,4H), 3.42 (m,2H), 2.6 (m2H).

By analogous procedure and using opportune intermediate prepared as described above, the following compounds can be prepared:

β-[1-methyl-4-[1-methyl-4-[1-methyl-4-[1-methyl-3-[4-N,N-bis(2-bromoethyl)amino-benzene-1-carboxamido] pyrazole-5-carboxamido]pyrrole-2-carboxamido]pyrrole-2-carboxamido]pyrrole-2-carboxamido]propionamidine, hydrobromide (Compound no. 76);

β-[1-methyl-3-[1-methyl-3-[1-methyl-4-[1-methyl-3-[4-N, N-bis(2-bromoethyl)amino-benzene-1-carboxamido] pyrazole-5-carboxamido]pyrrole-2-carboxamido] pyrazole-5-carboxamido]pyrazole-5-carboxamido] propionamidine, hydrobromide (Compound no. 77);

β-[1-methyl-3-[1-methyl-3-[1-methyl-4-[1-methyl-4-[4-N, N-bis(2-bromoethyl)amino-benzene-1-carboxamido] pyrrole-2-carboxamido]pyrrole-2-carboxamido]pyrazole-5-carboxamido]pyrazole-5-carboxamido] propionamidine, hydrobromide (Compound no. 78);

β-[1-methyl-3-[1-methyl-4-[1-methyl-4-[1-methyl-3-[4-N, N-bis(2-bromoethyl)amino-benzene-1-carboxamido] pyrazole-5-carboxamido]pyrrole-2-carboxamido]pyrrole-2-carboxamido]pyrazole-5-carboxamido] propionamidine, hydrobromide (Compound no. 79);

β-[1-methyl-3-[1-methyl-4-[1-methyl-4-[1-methyl-4-[4-N, N-bis(2-bromoethyl)amino-benzene-1-carboxamido] pyrrole-2-carboxamido]pyrrole-2-carboxamido]pyrrole-2-carboxamido]pyrazole-5-carboxamido] propionamidine, hydrobromide (Compound no. 80);

β-[1-methyl-3-[1-methyl-4-[1-methyl-3-[1-methyl-4-[4-N, N-bis(2-bromoethyl)amino-benzene-1-carboxamido] pyrrole-2-carboxamido]pyrazole-5-carboxamido]pyrrole-2-carboxamido]pyrazole-5-carboxamido] propionamidine, hydrobromide (Compound no. 81).

EXAMPLE 13

Intramuscular injection 10 mg/ml

An injectable pharmaceutical composition can be manufactured by dissolving 10 g of β-[1-methyl-3-[1-methyl-3-[1-methyl-4-[4-N,N-bis(2-chloroethyl)amino-benzene-1-carboxamido]pyrrole-2-carboxamido]pyrazole-5-carboxamido]pyrazole-5-carboxamido]propionamidine, hydrochloride in water for injection (1000 ml) and sealing ampoules of 1–5 ml.

EXAMPLE 14

Capsules, each dosed at 0.200 g and containing 10 mg of the active substance can be prepared as follows:

Composition for 500 capsules:

| | |
|---|---|
| β-[1-methyl-3-[1-methyl-3-[1-methyl-4-[4-N,N-bis (2-chloroethyl)amino-benzene-1-carboxamido]pyrrole-4-carboxamido]pyrazole-5-carboxamido]pyrazole-5-carboxamido]propionamidine hydrochloride | 5 g |
| Lactose | 85 g |
| Corn starch | 5 g |
| Magnesium stearate | 5 g |

This formulation can be encapsulated in two-piece hard gelatin capsules and dosed at 0.200 g for each capsule.

We claim:
1. A compound of formula (I)

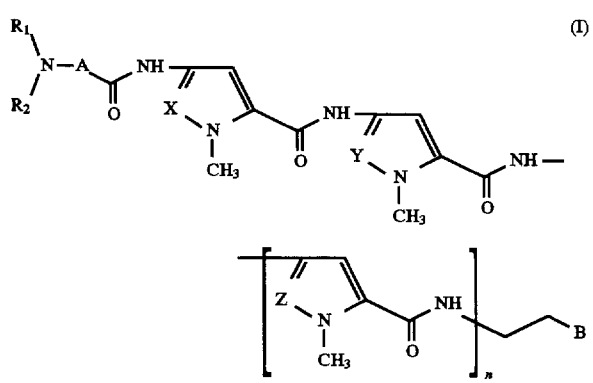

wherein n is 0 or 1;

each of X, Y, Z is independently N or CH;

A is a pentatomic heteromonocyclic ring unsubstituted or substituted by a $C_1$–$C_3$alkyl group;

B is

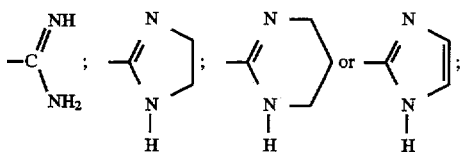

and either $R_1$ and $R_2$ are the same and they are both a $C_1-C_6$ alkyl group unsubstituted or substituted by halogen or hydroxy; or one of $R_1$ and $R_2$ is hydrogen and the other is a group

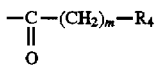

in which m is zero or an integer of 1 to 4 and $R_4$ is cyclopropyl; a vinyl group unsubstituted or substituted in position 1 or 2 by halogen or $C_1-C_3$ alkyl; or a group

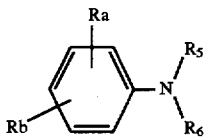

in which $R_5$ and $R_6$ are both a $C_1-C_6$ alkyl group unsubstituted or substituted by a halogen or hydroxy and in which each of $R_a$ and $R_b$ independently is hydrogen, $C_1-C_3$ alkyl or $C_1-C_3$ alkoxy; provided that:
a) where n=1, at least one of X, Y, and Z is a nitrogen atom; and
b) where n=0 and X and Y are CH, $R_1$ and $R_2$ are not the same and neither of $R_1$ and $R_2$ is a

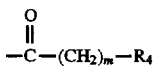

group wherein $R_4$ is a substituted or unsubstituted vinyl group or a group of formula

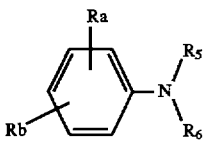

in which $R_a$, $R_b$, $R_5$ and $R_6$ are as defined above, or a pharmaceutically acceptable salt thereof.

2. A compound of formula (I) according to claim 1, wherein:
n is 0 or 1; each of X, Y, Z independently is N or CH;
A is thiazole, imidazole, 1,2,4-triazole, 1-methylpyrrole, 1-methylimidazole, 1-methylpyrazole;
B is

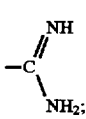

and either $R_1$ and $R_2$ are the same and they are both 2-chloroethyl, 2-fluoroethyl, 2-bromoethyl or one of $R_1$ and $R_2$ is hydrogen and the other is α-bromoacryloyl, 4-N,N-bis(2-chloroethyl)amino-benzene-1-carbonyl, 4-N,N-bis(2-bromoethyl)amino-benzene-1-carbonyl, provided that.

3. A compound selected from the group consisting of the following compounds:
β-[1-methyl-4-[1-methyl-4-[1-methyl-3-[4-N,N-bis(2-chloroethyl)amino-benzene-1-carboxamido]pyrrole-2-carboxamido]pyrrole-2-carboxamido]propionamidine;

β-[1-methyl-4-[1-methyl-4-[2-[4-N,N-bis(2-chloroethyl)amino-benzene-1-carboxamido]thiazole-4-carboxamido]pyrrole-2-carboxamido]pyrrole-2-carboxamido]propionamidine;

β-[1-methyl-3-[1-methyl-4-[1-methyl-4-[4-N,N-bis(2-chloroethyl)amino-benzene-1-carboxamido]pyrrole-2-carboxamido]pyrrole-2-carboxamido]pyrazole-5-carboxamido]propionamidine;

β-[1-methyl-3-[1-methyl-3-[1-methyl-4-[4-N,N-bis-(2-chloroethyl)amino-benzene-1-carboxamido]pyrrole-2-carboxamido]pyrazole-5-carboxamido]pyrazole-5-carboxamido]propionamidine;

β-[1-methyl-3-[1-methyl-4-[2-[4-N,N-bis(2-chloroethyl)amino-benzene-1-carboxamido]thiazole-4-carboxamido]pyrrole-2-carboxamido]pyrazole-5-carboxamido]propionamidine;

β-[1-methyl-4-[1-methyl-4-[3-[4-N,N-bis(2-chloroethyl)amino-benzene-1-carboxamido]triazole-5-carboxamido]pyrrole-2-carboxamido]pyrrole-2-carboxamido]propionamidine;

β-[1-methyl-3-[1-methyl-3-[1-methyl-3-[4-N,N-bis(2-chloroethyl)amino-benzene-1-carboxamido]pyrazole-5-carboxamido]pyrazole-5-carboxamido]pyrazole-5-carboxamido]propionamidine;

β-[1-methyl-4-[1-methyl-4-[1-methyl-4-[4-N,N-bis(2-chloroethyl)amino-benzene-1-carboxamido]imidazole-2-carboxamido]pyrrole-2-carboxamido]pyrrole-2-carboxamido]propionamidine;

β-[1-methyl-4-[1-methyl-3-[1-methyl-4-[4-N,N-bis(2-chloroethyl)amino-benzene-1-carboxamido]imidazole-2-carboxamido]pyrazole-5-carboxamido]pyrrole-2-carboxamido]propionamidine;

β-[1-methyl-4-[1-methyl-3-[3-[4-N,N-bis(2-chloroethyl)amino-benzene-1-carboxamido]-1,2,4-triazole-5-carboxamido]pyrazole-5-carboxamido]pyrrole-2-carboxamido]propionamidine;

β-[1-methyl-3-[1-methyl-3-[1-methyl-4-[4-N,N-bis(2-chloroethyl)amino-benzene-1-carboxamido]imidazole-2-carboxamido]pyrazole-5-carboxamido]pyrazole-5-carboxamido]propionamidine;

β-[1-methyl-3-[1-methyl-3-[3-[4-N,N-bis(2-chloroethyl)amino-benzene-1-carboxamido]-1,2,4-triazole-5-carboxamido]pyrazole-5-carboxamido]pyrazole-5-carboxamido]propionamidine;

β-[1-methyl-4-[1-methyl-4-[1-methyl-4-[1-methyl-3-[4-N,N-bis(2-chloroethyl)amino-benzene-1-carboxamido]pyrazole-5carboxamido]pyrrole-2-carboxamido]pyrrole-2-carboxamido]pyrrole-2-carboxamido]propionamidine;

β-[1-methyl-3-[1-methyl-3-[1-methyl-4-[1-methyl-3-[4-N,N-bis(2-chloroethyl)amino-benzene-1-carboxamido]pyrazole-5-carboxamido]pyrrole-2-carboxamido]pyrazole-5-carboxamido]pyrazole-5-carboxamido]propionamidine;

β-[1-methyl-3-[1-methyl-3-[1-methyl-3-[1-methyl-3-[4-N,N-bis(2-chloroethyl)amino-benzene-1-carboxamido]pyrazole-5-carboxamido]pyrazole-5-carboxamido]pyrazole-5-carboxamido]pyrazole-5-carboxamido]propionamidine;

β-[1-methyl-4-[1-methyl-4-[2(α-bromoacrylamido)thiazole-4-carboxamido]pyrrole-2-carboxamido]pyrrole-2-carboxamido]propionamidine;

β-[1-methyl-4-[1-methyl-4-[1-methyl-3-[α-bromoacrylamido)pyrazole-5-carboxamido]pyrrole-2-carboxamido]pyrrole-2-carboxamido]propionamidine;

β-[1-methyl-4-[1-methyl-4-[3-(α-bromoacrylamido)-1,2,4-triazole-5-carboxamido]pyrrole-2-carboxamido]pyrrole-2-carboxamido]propionamidine;

β-[1-methyl-3-[1-methyl-3-[1-methyl-4-(α-bromoacrylamido)pyrrole-2-carboxamido]pyrazole-5-carboxamido]pyrazole-5-carboxamido]propionamidine;

β-[1-methyl-3-[1-methyl-4-[1-methyl-4-(α-bromoacrylamido)pyrrole-2-carboxamido]pyrrole-2-carboxamido]pyrazole-5-carboxamido]propionamidine;

β-[1-methyl-3-[1-methyl-4-[2-(α-bronoacrylamido)thiazole-4-carboxamido]pyrrole-2-carboxamido]pyrazole-5-carboxamido]propionamidine;

β-[1-methyl-4-[1-methyl-4-[1-methyl-4-(α-bromoacrylamido)imidazole-2-carboxamido]pyrrole-2-carboxamido]pyrrole-2-carboxamido]propionamidine;

β-[1-methyl-3-[1-methyl-3-[1-methyl-3-(α-bromoacrylamido)pyrazole-5-carboxamido]pyrazole-5-carboxamido]pyrazole-5-carboxamido]propionamidine;

β-[1-methyl-4-[1-methyl-3-[1-methyl-4-(α-bromoacrylamido)imidazole-2-carboxamido]pyrazole-5-carboxamido]pyrrole-2-carboxamido]propionamidine;

β-[1-methyl-4-[1-methyl-3-[3-(α-bromoacrylamido)-1,2,4-triazole-5-carboxamido]pyrrole-5-carboxamido]pyrazole-2-carboxamido]propionamidine;

β-[1-methyl-4-[1-methyl-4-[1-methyl-3-[1-methyl-3-(α-bromoacrylamido)pyrazole-5-carboxamido]pyrazole-5-carboxamido]pyrrole-2-carboxamido]pyrrole-2-carboxamido]propionamidine;

β-[1-methyl-3-[1-methyl-3-[1-methyl-3-[1-methyl-3-(α-bromoacrylamido)pyrazole-5-carboxamido]pyrazole-5-carboxamido]pyrazole-5-carboxamido]pyrazole-5-carboxamido)propionamidine;

β-[1-methyl-4-[1-methyl-4-[1-methyl-4-[1-methyl-3-(α-bromoacrylamido)pyrazole-5-carboxamido]pyrrole-2-carboxamido]pyrrole-2-carboxamido]pyrrole-2-carboxamido]propionamidine;

β-[1-methyl-4-[1-methyl-4-[1-methyl-3-[1-methyl-3-[4-N,N-bis(2-chloroethyl)amino-benzene-1-carboxamido]pyrazole-5-carboxamido]pyrazole-5-carboxamido]pyrrole-2-carboxamido]pyrrole-2-carboxamido]propionamide;

β-[1-methyl-4-[1-methyl-4-[1-methyl-4-[2-[4-N,N-bis(2-chloroethyl)amino-benzene-1-carboxamido]thiazole-4-carboxamido]pyrrole-2-carboxamido]pyrrole-2-carboxamido]propionamidine;

β-[1-methyl-4-[1-methyl-4-[1-methyl-4-[1-methyl-4-[4-N,N-bis(2-chloroethyl)amino-benzene-1-carboxamido]imidazole-2-carboxamido]pyrrole-2-carboxamido]pyrrole-2-carboxamido]pyrrole-2-carboxamido]propionamidine;

β-[1-methyl-4-[1-methyl-4-[1-methyl-4-[3-[4-N,N-bis(2-chloroethyl)amino-benzene-1-carboxamido]1,2,4-triazole-5-carboxamido]pyrrole-2-carboxamido]pyrrole-2-carboxamido]propionamidine;

β-[1-methyl-3-[1-methyl-3-[2-[4-N,N-bis(2-chloroethyl)amino-benzene-1-carboxamido]thiazole-4-carboxamido]pyrazole-5-carboxamido]pyrazole-5-carboxamido]propionamidine;

β[1-methyl-4-[1-methyl-4-[1-methyl-3-[1-methyl-4-[4-N,N-bis(2-chloroethyl)amino-benzene-1-carboxamido]imidazole-2-carboxamido]pyrazole-5-carboxamido]pyrrole-2-carboxamido]pyrrole-2-carboxamido]propionamidine;

β-[1-methyl-4-[1-methyl-4-[1-methyl-3-[1-methyl-4-[4-N,N-bis(2-chloroethyl)amino-benzene-1-carboxamido]pyrrole-2-carboxamido]pyrazole-5-carboxamido]pyrrole-2-carboxamido]pyrrole-2-carboxamido]propionamidine;

β-[1-methyl-4-[1-methyl-3-[1-methyl-3-(4-N,N-bis(2-chloroethyl)amino-benzene-1-carboxamido]pyrazole-5-carboxamido]pyrazole-5-carboxamido]pyrrole-2-carboxamido]propionamidine;

β-[1-methyl-4-[1-methyl-3-[1-methyl-4-[4-N,N-bis(2-chloroethyl)amino-benzene-1-carboxamido]pyrazole-5-carboxamido]pyrrole-2-carboxamido]pyrrole-2-carboxamido]propionamidine;

β-(1-methyl-4-(1-methyl-3-(1-methyl-4-(α-bromoacrylamido)pyrrole-2-carboxamido)pyrazole-5-carboxamido)pyrrole-2-carboxamido)propionamidine;

β-(1-methyl-4-(1-methyl-3-(1-methyl-3-(α-bromoacrylamido)pyrazole-5-carboxamido)pyrazole-5-carboxamido)pyrrole-2-carboxamido)propionamidine;

β-(1-methyl-4-(1-methyl-4-(1-methyl-3-(1-methyl-4-(α-bromoacrylamido)pyrrole-2-carboxamido)pyrazole-5-carboxamido)pyrrole-2-carboxamido)pyrrole-2-carboxamido)propionamidine;

β-(1-methyl-4-(1-methyl-4-(1-methyl-3-(1-methyl-4-(α-bromoacrylamido)imidazole-2-carboxamido)pyrazole-5-carboxamido)pyrrole-2-carboxamido)pyrrole-2-carboxamido)propionamidine;

β-[1-methyl-4-[1-methyl-4-[1-methyl-3-[4-N,N-bis(2-bromoethyl)amino-benzene-1-carboxamido]pyrazole-5-carboxamido]pyrrole-2-carboxamido]pyrrole-2-carboxamido]propionamidine;

β-[1-methyl-3-[1-methyl-4-[1-methyl-4-[4-N,N-bis(2-bromoethyl)amino-benzene-1-carboxamido]pyrrole-2-carboxamido]pyrrole-2-carboxamido]pyrazole-5-carboxamido]propionamidine;

β-[1-methyl-3-[1-methyl-3-[1-methyl-4-[4-N,N-bis(2-bromoethyl)amino-benzene-1-carboxamido]pyrrole-2-carboxamido]pyrazole-5-carboxamido]pyrrole-5-carboxamido]propionamidine;

β-[1-methyl-4-[1-methyl-4-[1-methyl-4-[1-methyl-3-[4-N,N-bis(2-bromoethyl)amino-benzene-1-carboxamido]pyrazole-5-carboxamido]pyrrole-2-carboxamido]pyrrole-2-carboxamido]pyrrole-2-carboxamido]propionamidine;

β-[1-methyl-3-[1-methyl-3-[1-methyl-4-[1-methyl-3-[4-N,N-bis(2-bromoethyl)amino-benzene-1-carboxamido]pyrazole-5-carboxamido]pyrrole-2-carboxamido]pyrazole-5-carboxamido]pyrazole-5-carboxamido]propionamidine;

β-[1-methyl-3-[1-methyl-3-[1-methyl-4-[1-methyl-4-(4-N,N-bis(2-bromoethyl)amino-benzene-1-carboxamido]pyrrole-2-carboxamido]pyrrole-2-carboxamido]pyrazole-5-carboxamido]pyrazole-5-carboxamido]propionamidine;

β-[1-methyl-3-[1-methyl-4-[1-methyl-4-[1-methyl-3-[4-N,N-bis(2-bromoethyl)amino-benzene-1-carboxamido]pyrazole-5-carboxamido]pyrrole-2-carboxamido]pyrrole-2-carboxamido]pyrazole-5-carboxamido]propionamidine;

β-[1-methyl-3-[1-methyl-4-[1-methyl-4-[1-methyl-4-[4-N,N-bis(2-bromoethyl)amino-benzene-1-carboxamido]pyrrole-2-carboxamido]pyrrole-2-carboxamido]pyrrole-2-carboxamido]pyrazole-5-carboxamido]propionamidine;

β-[1-methyl-3-[1-methyl-3-[1-methyl-3-[1-methyl-4-[4-N,N-bis(2-bromoethyl)amino-benzene-1-carboxamido]pyrrole-2-carboxamido]pyrazole-5-carboxamido]pyrrole-2-carboxamido]pyrazole-5-carboxamido]propionamidine, and the pharmaceutically acceptable salts thereof.

4. A compound as recited in claim 3, wherein said compound is β-[1-methyl-3-[1-methyl-4-[1-methyl-4-[4-N, N-bis-(2-chloroethyl)amino-benzene-1-carboxamido]pyrrole-2-carboxamido]pyrrole-2-carboxamido]pyrazole-5-carboxamido]propionamidine.

5. A compound as recited in claim 3, wherein said compound is β-[1-methyl-3-[1-methyl-3-[1-methyl4-[4-N,N-bis-(2-chloroethyl)amino-benzene-1-carboxamido]pyrrole-2-carboxamido]pyrazole-5-carboxamido]pyrazole-5-carboxamido]propionamidine.

6. A compound as recited in claim 3, wherein said compound is β-[1-methyl-3-[1-methyl-3-[1-methyl-4-[4-N,N-bis-(2-bromoethyl)amino-benzene-1-carboxamido]pyrrole-2-carboxamido]pyrazole-5-carboxamido]pyrazole-5-carboxamido]propionamidine.

7. A compound of formula (I)

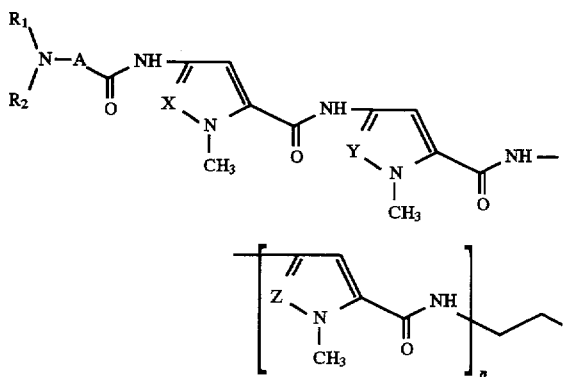

(I)

wherein n is 0 or 1;

each of X, Y, Z is independently N or CH;

A is a pentatomic heteromonocyclic ring unsubstituted or substituted by a $C_1$–$C_3$ alkyl group;

B is

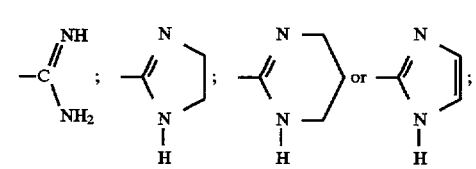

and either $R_1$ and $R_2$ are the same and they are both a $C_1$–$C_6$ alkyl group unsubstituted or substituted by halogen or hydroxy; or one of $R_1$ and $R_2$ is hydrogen and the other is a group

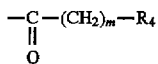

in which m is zero or an integer of 1 to 4 and $R_4$ is cyclopropyl; a vinyl group unsubstituted or substituted in position 1 or 2 by halogen or $C_1$–$C_3$ alkyl; or a group

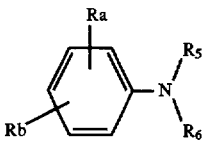

in which $R_5$ and $R_6$ are both a $C_1$–$C_6$ alkyl group unsubstituted or substituted by a halogen or hydroxy and in which each of $R_a$ and $R_b$ independently is hydrogen, $C_1$–$C_3$ alkyl or $C_1$–$C_3$ alkoxy; provided that:

a) where n=1, at least one of X, Y, and Z is a nitrogen atom; and b) where n=0, at least one of X and Y is a nitrogen atom, or a pharmaceutically acceptable salt thereof.

8. A method of making a pharmaceutical composition comprising combining a compound of formula (I) according to claim 1 and a pharmaceutically acceptable excipient.

9. A process for preparing a compound of formula (I) according to claim 1, or a pharmaceutically acceptable salt thereof, comprising:

a) reacting a compound of formula (II)

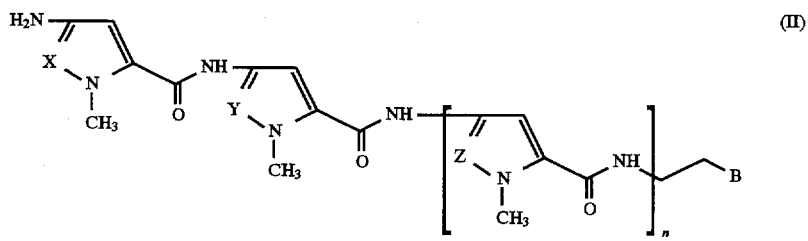

(II)

wherein X, Y, Z, B and n are as defined in claim 1 or a salt thereof with a compound of formula (III)

(III)

wherein $R_1$, $R_2$ and A are as defined in claim 1 and W is hydroxy or a leaving group; or b) reacting a compound of formula (IV)

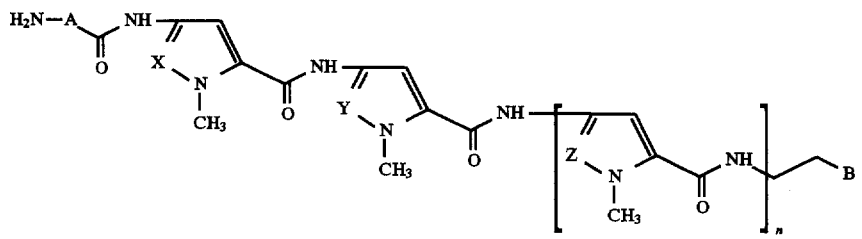
(IV)

wherein A, X, Y, Z, B and n are as defined in claim 1 or a salt thereof with a compound of formula (V)

R₁—W (V)

wherein R₁ is as defined in claim 1 and W is as defined above so obtaining a compound of formula (I) wherein R₁ is as defined in claim 1 and R₂ is hydrogen or is the same as R₁ and, if desired salifying a compound of formula (I) or obtaining a free compound from a salt, and/or, if desired, separating a mixture of isomers of formula (I) into the singleisomers.

10. A pharmaceutical composition comprising a compound of formula (I), or a pharmaceutically acceptable salt thereof, according to claim 1, as the active principle, and a pharmaceutically acceptable carrier and/or diluent.

11. A method of treating a tumor in a patient in need of treatment of a tumor, comprising administering to the patient an anti-tumor effective amount of a compound of formula (I) according to claim 1.

12. A method of treating a tumor in a patient in need of treatment of a tumor, comprising administering to the patient an anti-tumor effective amount of a composition according to claim 10.

* * * * *